United States Patent [19]
Albagli et al.

[11] Patent Number: 6,004,513
[45] Date of Patent: *Dec. 21, 1999

[54] AUTOMATIC DEVICE FOR NUCLEIC ACID SEQUENCE DETECTION EMPLOYING AMPLIFICATION PROBES

[75] Inventors: David Albagli, Palo Alto; Reuel VanAtta, Mountain View; Michael Wood, Palo Alto, all of Calif.

[73] Assignee: Naxcor, Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/577,121

[22] Filed: Dec. 22, 1995

Related U.S. Application Data

[63] Continuation-in-part of application No. 08/487,034, Jun. 7, 1995, Pat. No. 5,767,259, which is a continuation-in-part of application No. 08/364,339, Dec. 27, 1994, Pat. No. 5,616,464.

[51] Int. Cl.⁶ .............................. G01N 15/06; C12Q 1/68
[52] U.S. Cl. .............................................. 422/68.1; 435/6
[58] Field of Search .............................. 435/6, 91.1, 91.2, 435/286.1, 303.1; 422/64, 67, 104, 105, 109

[56] References Cited

U.S. PATENT DOCUMENTS

| | | | |
|---|---|---|---|
| 4,851,330 | 7/1989 | Kohne | 435/6 |
| 4,883,750 | 11/1989 | Whiteley et al. | 435/6 |
| 4,965,188 | 10/1990 | Mullis et al. | 435/6 |
| 5,185,243 | 2/1993 | Ullman | 435/6 |
| 5,219,734 | 6/1993 | Royer et al. | 435/6 |
| 5,449,602 | 9/1995 | Royer et al. | 435/6 |
| 5,475,610 | 12/1995 | Atwood et al. | 364/500 |
| 5,602,756 | 2/1997 | Atwood et al. | 364/500 |
| 5,616,301 | 4/1997 | Moser et al. | 422/104 |
| 5,629,149 | 5/1997 | Santamaria et al. | 435/6 |

FOREIGN PATENT DOCUMENTS

| | | |
|---|---|---|
| 0 097 373 B1 | 1/1984 | European Pat. Off. . |
| 0 320 308 B1 | 6/1989 | European Pat. Off. . |
| 0 336 731 B1 | 5/1994 | European Pat. Off. . |
| 0 324 616 B1 | 3/1995 | European Pat. Off. . |
| WO 90/01069 | 7/1989 | WIPO . |
| WO 94/29485 | 6/1994 | WIPO . |
| 94/29485 | 12/1994 | WIPO . |

OTHER PUBLICATIONS

Guatelli et al., "Isothermal, In Vitro Amplification of Nucleic Acids by a Multienzyme Reaction Modeled After Retroviral Replication," PNAS (1990), 87:1874–1878.

Barany, "Genetic Disease Detection and DNA Amplification Using Cloned Thermostable Ligase," PNAS (1991), 88:189–193.

*Primary Examiner*—Eggerton A. Campbell
*Attorney, Agent, or Firm*—Flehr Hohbach Test Albritton & Herbert LLP; Richard F. Trecartin

[57] ABSTRACT

Methods and compositions are provided for detecting nucleic acid sequences. In particular, pairs of probes are employed, where the pair defines a substantially contiguous sequence on a target nucleic acid. Each of the pairs has a side chain which forms a stem of the two side chains which non-covalently binds and is capable of forming a cross-link upon activation, when the probes and sample nucleic acid are base paired. Cross-linking of the stems when unbound to complementary DNA is inhibited. Each of the nucleic acids is initially present as single stranded nucleic acid to allow for base pairing, so that the probes bind to homologous target nucleic acid. The assay mixture is activated to provide cross-linking, the double stranded nucleic acid melted, and the process of base pairing, activation and melting repeated, a sufficient number of cycles, to provide a detectable amount of cross-linked probes. To inhibit background cross-linking, the side chains may provide for duplex formation, where a portion of the side chain binds to a different portion of the side chain or the portion of the probe homologous to the target. Also provided are kits comprising reagents, as well as automatic devices, for carrying out the subject method.

5 Claims, 4 Drawing Sheets

AUTOMATIC DEVICE FOR NUCLEIC ACID SEQUENCE DETECTION EMPLOYING AMPLIFICATION PROBES

CROSS-REFERENCE TO RELATED APPLICATIONS

This application is a continuation-in-part of Ser. No. 08/487,034, filed Jun. 7, 1995, U.S. Pat. No. 5,767,259 on Jun. 16, 1998 which is a continuation-in-part of application Ser. No. 08/364,339 filed Dec. 27, 1994 patented and issued as U.S. Pat. No. 5,616,464 on Apr. 1, 1997, the disclosure of which is herein incorporated by reference.

INTRODUCTION

1. Technical Field

The field of this invention is nucleic acid sequence detection.

2. Background

The amount of information concerning the genomes of a large variety of species is increasing exponentially. The availability of known sequences creates an enormous market for the detection of particular sequences present as DNA or RNA, whereby one can detect the presence of genes, their transcription or mutations, such as lesions, substitutions, deletions, translocations, and the like. By knowing sequences of interest, one can detect a wide variety of pathogens, particularly unicellular microorganisms and viral strains, and genetic diseases including the presence of genes imparting antibiotic resistance to the unicellular microorganisms, as illustrative of only a few of the available possibilities. In addition, there are needs within the extensive areas of genetic counseling, forensic medicine, research, and the like, for nucleic acid sequence detection technology.

In many instances, the target nucleic acid sequence is only a very small proportion of total nucleic acid in the sample. Furthermore, there may be many situations where the target nucleic acid of interest and other sequences present have substantial homology. It is therefore important to develop methods for the detection of the target nucleic acid sequence that are both sensitive and accurate.

Several enzymatic amplification methods have been developed, such as the polymerase chain reaction (PCR), the ligase chain reaction (LCR), NASBA, and self-sustained sequence replication (SSR). The first and most notable method that has received extensive use is PCR. Starting with specific primers, nucleoside triphosphate monomers, the target strand of DNA and a polymerase enzyme, one can greatly amplify the target DNA sequence of interest. This technology is extremely powerful and has been applied to a myriad of research applications, but it has a number of drawbacks which limit its use in a variety of areas. General availability is limited by the restrictive nature of licenses by the owners of the patent rights. In addition, the method requires an enzyme. While the availability of thermally stable enzymes has greatly enhanced the applicability of PCR, there is nevertheless the inconvenience that denaturation of the enzyme occurs during thermocycling. Also, the sample may include inhibitors of the enzyme requiring isolation of the nucleic acid sample free of inhibiting components. In addition, the methodology is sensitive to amplifying stray sequences, which then overwhelm the target sequence of interest, obscuring its presence. There is also the fact that the reagents are expensive and the amplified DNA usually requires verification. These comments apply equally to the other enzymatic amplified techniques noted above, such as LCR, NASBA, and SSR.

There is, therefore, substantial interest in identifying alternative techniques which allow for the detection of specific DNA sequences and avoid the deficiencies of the other systems. Also of interest is the development of devices for automatically carrying out these alternative nucleotide sequence detection techniques, where these automatic devices will reduce the opportunity of error introduction and provide for consistency of assay conditions.

Relevant Literature

Barany, Proc. Natl. Acad. Sci. USA (1991) 88: 189–193; Gautelli et al., Proc. Natl. Acad. Sci. USA (1990) 87: 1874–1878. Segev Diagnostics, Inc. WO 90/01069. Imclone Systems, Inc. WO 94/29485. U.S. Pat. Nos. 5,185,243, 4,683,202 and 4,683,195.

SUMMARY OF THE INVENTION

Methods and compositions are provided for detecting nucleic acid sequences by using a pair of probes, in each of which at a different end there is a portion of the chain which serves as one half of a stem, which portion will be referred to as a side chain. The side chains comprise a cross linking system, which has a photoactivatable entity, normally coupled to a passive reactive entity. Upon orientation of the side chains in spacial proximity as a result of binding of the probes to a contiguous homologous target sequence and activation of the cross linking system associated with the side chains, the probes are joined together by a covalent linkage. The method employs adding the probes to the target nucleic acid under conditions of base pairing, activating the cross-linking system, so that primarily only those side chains in spacial proximity form a covalent bond, melting double-stranded nucleic acid and repeating the cycle. Where only one set of probes is used, the expansion is linear; where complementary sets of probes are used, in the re-annealing process the probes in addition to binding to target nucleic acid, will also bind to cross-linked probes. In this manner, one may obtain a linear or geometric increase in the number of cross-linked probes as the cycle of steps is repeated, wherein the process is initiated by the presence of target DNA.

In a preferred embodiment, the probes have non-cross-linking duplex forming side chains, where at least one side chain is in the form of a duplex prior to hybridization with the target DNA. The side chains are characterized that at least one of the side chains has a photoactivatable group and the other of the side chains has a recipient group which reacts with the photoactivatable group to form a covalent bond.

The methods comprise combining the probes whose sequences are homologous to adjacent sequences in the target DNA under conditions, which may be successive or simultaneous, which result in melting of the side chain duplexes and hybridization of the probes to the target DNA. After sufficient time for hybridization between the probes and the target DNA to occur, the hybridization medium is irradiated to photoactivate the photoactivatable groups, which will react with the recipient group to cross-link the probes bound to target DNA or dimerized probes.

DESCRIPTION OF THE SPECIFIC EMBODIMENTS

Figure 1:
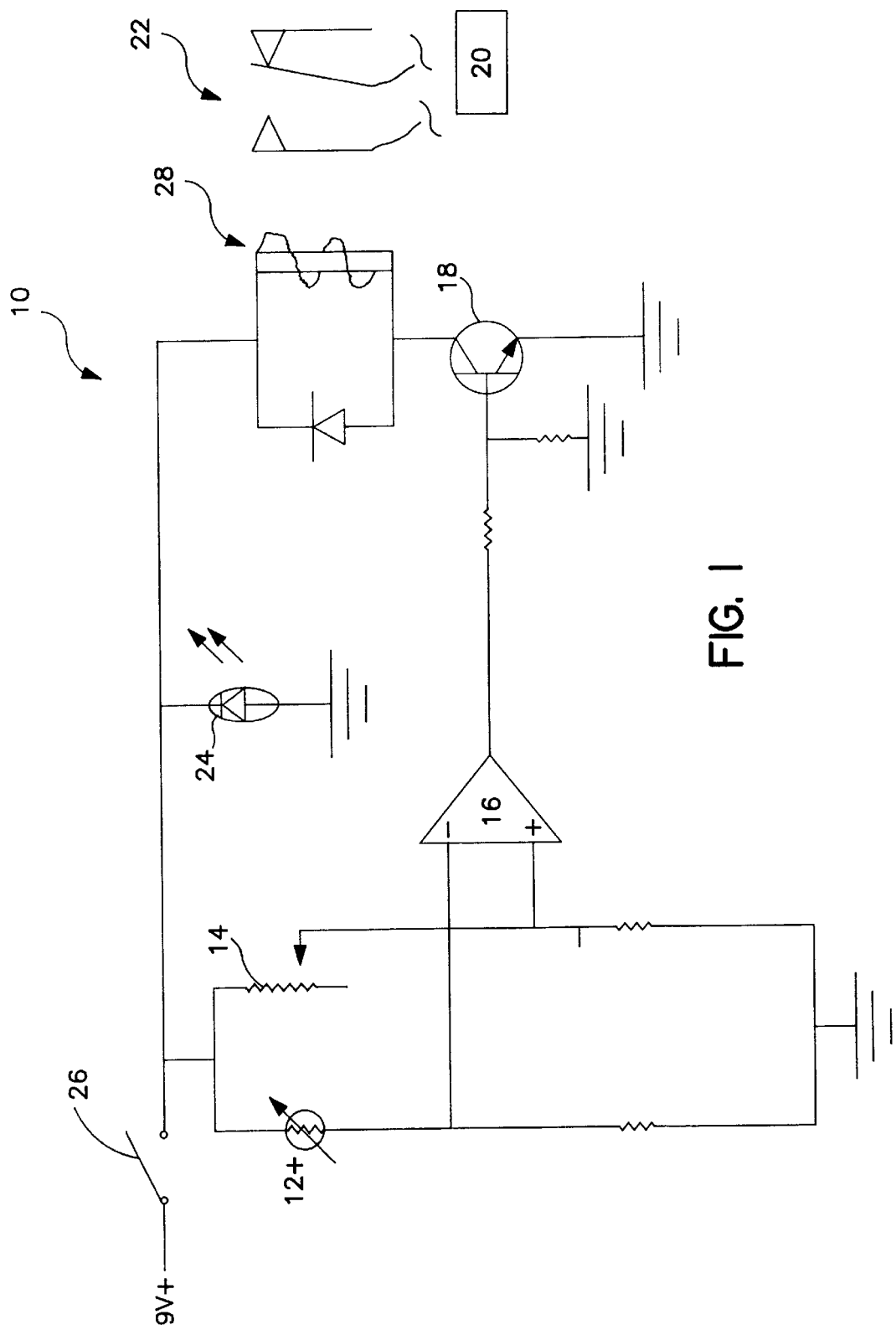
FIG. 1 is a block diagram of a first embodiment of a control circuit of an automatic device according to the subject invention.

Methods and compositions are provided for detecting a nucleic acid sequence employing at least one set comprising a pair of first and second probes. The pair of probes defines a target sequence, where upon base pairing of the probes to the target sequence, the probes are brought into close spacial proximity. Each of the probes has a portion of the probe, which acts as a side chain which does not bind to the target sequence. The side chains act as one-half of a stem and non-covalently interact through hydrogen bonding, salt bridges, and/or Van der Waal forces. When the stem is formed, the side chains comprise a covalent bond cross-linking system, which upon activation results in a covalent bond between the side chains, thus permanently linking the probes under the conditions of the process.

The method is performed by combining the target nucleic acid with the pair of probes or sets of probe pairs in an appropriate medium for base pairing to produce an assay medium. The nucleic acid may be DNA or RNA, single or double stranded, or other molecule which comprises pyrimidines and/or purines or their analogs capable of base pairing. After sufficient time for the probes to bind to the target nucleic acid or in subsequent steps to bind as well to cross-linked probes, the cross-linking system is activated resulting in covalent bonding between the two probes. One then melts double stranded nucleic acid to release the probes from the homologous sequence and repeats the process over again, whereby the number of cross-linked probes in the presence of target sequence is increased linearly or geometrically. Where only one set of probes is used, linear amplification of cross-linked probes is obtained, which may be satisfactory in many instances.

In describing the subject invention, the probes will be considered first. Each of the probes will have a sequence of at least about 10, more usually at least about 15, preferably at least about 18 and usually not more than about 1 kb, more usually not more than about 0.5 kb, preferably in the range of about 18 to 200 nt, and frequently not more than 60 nucleotides, where the sequence is homologous to the target sequence. For the most part, the total number of nucleotides which are homologous to the target sequence for the two probes will be at least about 15 nt, more usually at least about 25 nt, and not more than about 1.2 kb, usually not more than about 0.5 kb, preferably not more than about 300 nt. The base pairing domains present on the target nucleic acid will normally not be separated by more than 10 nt, more usually not more than about 6 nt, and preferably not more than about 2 nt and may be contiguous.

Desirably, particularly where the side chain is involved with duplex formation ("duplexed side chain"), the probe with the side chain having the photoactivatable group will desirably have a fewer number of complementary nucleotides to the target as compared to the probe having the recipient group. In this way, where only one probe has hybridized to the target, it will more likely be the probe with the recipient group, which will not react with the target upon photoactivation.

Each of the probes has a side chain, 3' on the first probe and 5' on the second probe in the 5'-3' direction, which will provide for non-covalent association to form a stem. Non-covalent association can be obtained by hydrogen bonding, salt bridges, Van der Waal forces, and the like, particularly hydrogen bonding. For the most part, the groups involved for association will have oxygen and nitrogen bonded hydrogen, e.g. purines and pyrimidines. Upon activation, covalent cross-linking between members of the stem occurs. The reaction rate occurring as a result of the spacial proximity of the side chains due to the base pairing of the probes to a homologous sequence will usually be at least about 10 fold, preferably at least about 100 fold, greater than the reaction that occurs between the probes unbound to the homologous sequence.

The side chains will be selected so as to have a weak association or affinity. By weak is intended that in the absence of the target in the solution, the equilibrium between unassociated probes in solution and associated probes, due to the affinity between the side chains and target homologous nucleic acid sequences will be less than about $10^{-1}$, usually less than about $10^{-3}$ $M^{-1}$. The affinity may be as a result of hydrogen bonding, salt formation, or other low energy event.

To obtain stem formation, conveniently, one may use paired nucleotides, at least 2, generally at least 3, and usually not more than about 20, more usually not more than about 16 base pairs, preferably not more than about 8 base pairs, more preferably not more than about 6 base pairs, usually in the range of 2 to 6 base pairs, more usually in the range of 4 to 6 base pairs. Alternatively, one may use amino acids which provide for hydrogen bonding and/or salt bridges. Other hydrogen bridges may involve diamines and diol acidic groups, particularly ortho-phenolates. However, for the most part, considering convenience, ease of synthesis, control of affinity, and substantial absence of interference, nucleotides, nucleotide analogues or derivatives will be employed, for example, where the sugars or phosphates may be substituted, base amino and oxo groups modified, and the like. Usually, the pairs will be A and T, where the nucleotides may be the same on one side chain or different, that is all Ts on one chain and all As on the other chain, or a mixture of As and Ts on the two side chains. However, one may also use G and C, by themselves or in combination with A and T. Instead of the normal 4 or 5 natural bases (including uracil), one may use other bases or other moieties providing for hydrogen bonding and spacial orientation, such as 5-methylcytosine, 5-fluorouracil, 2'-deoxy-5-(trifluoromethyl)uridine, inosine, 1-methylinosine, 3-nitropyrrole, and the like. The particular choice of nucleotide or substitute moiety will depend on the desired affinity, ease of synthesis, interaction with the covalent cross-linking, opportunity to serve as a reactant for cross-linking, and the like. Generally, the side chains, excluding groups bound to the chain will be at least about 20 atoms in the chain, more usually at least about 30 atoms in the chain, generally fewer than 100 atoms, more usually fewer than about 60 atoms. The atoms will be carbon, oxygen, nitrogen, sulfur, phosphorus, and the like. The cross-linking moieties may be part of the side chain or appended to the side chain, depending upon the nature of the moiety.

The base pairing sequences of the two probes will be selected so as to provide a low affinity between the two probes. Therefore, the target sequences will be selected so that there will not be a significant number of nucleotides defining a sequence of homology, particularly complementarity, between the two probes. The greater the complementarity between the two probes, the more stringent the conditions will be required during the period of activation of the cross-linking system. Therefore, one has substantial discretion in the selection of the probes in relation to the conditions employed for base pairing of the homologous sequences.

The orientation of the stems may be varied, so that the stems may be in the same or opposite orientation to the target complementary sequence. Thus, one of the stems may be in a parallel orientation to provide for Hoogsten base pairing, or both may have anti-parallel orientation, so as to have 3'-3' coupling of one stem to the target complementary sequence and analogously 5'-5' coupling of the other stem to the target complementary sequence.

For geometric expansion, the target complementary portion of the probes need not, and preferably will not, have target complementary regions of the same length. Therefore, when the two complementary probes of the two sets are hybridized, a portion of the target complementary regions will be exposed generally of from 1 to 10, usually of from about 2 to 6, nucleotides. The exposed portion will be of the 5' probe in one combination of probes and the 3' portion in the other combination. When the four probes are hybridized, all of the complementary regions will be hybridized, where a 5' probe in one combination will extend over the 3' probe of the other combination.

In one embodiment, one of the side chains will provide for a bulge adjacent to the homologous sequence. The bulge will be between the last nucleotide base pairing with the target sequence and directly linked to said side chain and the first group providing for non-covalent association between the side chains to form the stem, e.g. base pairing of nucleotides on respective side chains. Using nucleotides as exemplary, there will usually be 1 to 3 unpaired nucleotides, before base pairing occurs between the two side chains. Other groups may be used which provide approximately the same degree of flexibility. There will usually be only one bulge, but in some situations, one may have a bulge in each side chain.

Both of the members involved in the cross-linking will normally be provided by an intermediate, at least one of which is not a nucleotide or modified nucleotide, although in some situations one of the members may be a nucleotide or modified nucleotide. By employing a difunctional molecule for insertion into the chain of the side chain, where the difunctional molecule carries the cross-linking agent, the members of the side chains participating in the cross-linking may be conveniently positioned for reaction. Various polyfunctional molecules may be used to provide stable participation of the cross-linking moiety in the side chain. Desirably, agents will be used which can react with a phosphorus moiety, particularly a phosphoramidite, or can form a phosphoramidite, where the linking atom may be oxygen, carbon, sulfur, or the like. Core molecules for linking a cross-linking moiety to the side chain, where the core molecule participates in the backbone of the side chain, include glycerol, dithiothreitol, 1,3,5-trihydroxycyclohexane, deoxyribose, 2-hydroxymethylacrylic acid, or the like. Since the phosphorus group can be modified to react with a wide variety of functionalities, there is no significant restriction on how the core molecule is fitted into the backbone of the side chain. Phosphorus derivatives include, phosphoramidites, phosphate esters, phosphines, phosphohalides, etc.

In order to reduce the amount of cross-linking of probes in the absence of being bound to the target molecule, protective systems are provided. The protective system may employ duplex formation, where the duplex may be solely associated with a side chain, associated with a sequence of the probe homologous to the target, or a side chain associated with an additional molecule. The duplex may form a hairpin (which includes a stem and loop), where a hairpin has at least three unmatched contiguous nucleotides. Usually not more than about 8, more usually not more than about 5, of the nucleotides are unmatched. By hairpin is intended that the turn to form the duplex has at least three nucleotides which are unmatched. By stem and loop is intended that there is more than three unmatched nucleotides at the turn to form the loop. By a bulge is intended that there are unmatched nucleotides along the stem, which results in a bulge. Usually, if there is only one duplex forming side chain, it will be the side chain with the recipient or passive reactive group.

Figure 4A:
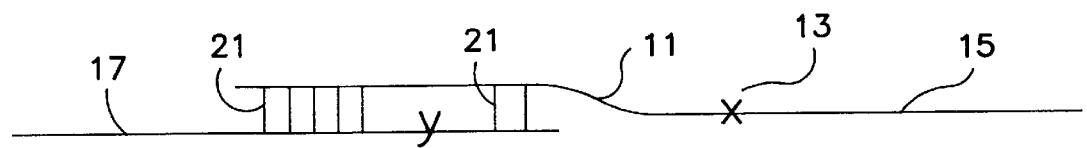
FIG. 4A shows a first protective system with side chains hybridized and FIG. 4B shows a first protective system with two probes bound to the target.
Figure 4B:
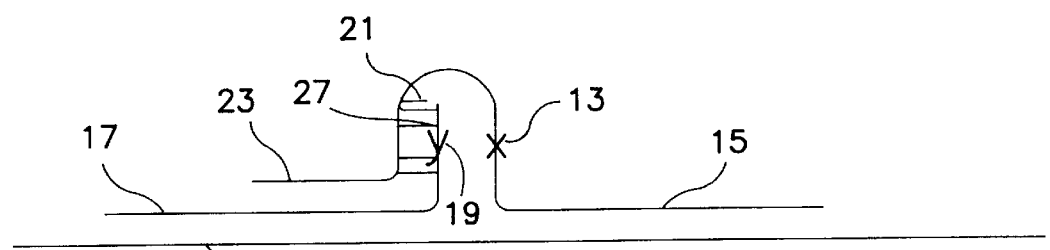

The first protective system has the terminal sequence of one side chain complementary in the reverse order, so that the hybridizing sequences are both in the 5'-3' direction as shown in FIG. 4. The hybridizing sequence of one side chain 11 has a cross-linking group 13 which comprises a member of the cross-linking system. In considering how the two probes, the 3' probe 15 and the 5' probe 17 will exist in solution if the side chains hybridize, as shown in the FIG. 4A, one should picture the stems forming dsDNA, where the 5' probe 17 has the member of the cross-linking system Y 19 in the hybridizing portion of the side chain, while the 3' probe 15 has the member of the cross-linking system X 13 distal to the hybridizing portion. The vertical lines 21 indicate base pairing. The 3' probe 15 is shown as extended so as to hybridize to the sequence of the 5' probe complementary to the target, allowing for triplex formation 23 when the probes are bound to the target 25. The portion of the stem complementary to the target hybridizing portion will usually not exceed five nucleotides, usually not exceeding three nucleotides. In FIG., 4B, the two probes are bound to the target 25. The 3' probe stem 11 is hybridized to the 5' probe stem 27, while the 3' probe is hybridized to the target, pulling the linking group around and the cross-linking member of the 3' probe 13 into juxtaposition to the 5' probe cross-linking member 19.

By removing a member of the cross-linking system out of the hybridizing region of the stem, even when the stems are hybridized, the probability of obtaining cross-linking without being bound to target is substantially diminished. Furthermore, by having unreactive groups opposite the photoactivatable group in the hairpin, upon photoactivation, there will be no reaction. For example, by using an unreactive group, such as an unsubstituted sugar, dihydrothymidine, pseudouridine, and the like, as the unit across from the photoactivatable group, the photoactivated group will not have a partner with which to react and will return to the ground state from the photoactivated state to be available for a future reaction with a recipient group.

The linking chain which joins the stem forming sequence to the target homologous sequence of the probe may comprise any linking system which does not interfere with the purposes of the probe and is convenient from a synthetic standpoint. Desirably, the linking chain is hydrophilic and may be a polyether, polyester, polypeptide, polyamine, etc. Thus the linking chain may comprise alkyleneoxy, wherein alkylene will generally be of from 1 to 3 carbon atoms and the total number of alkylene groups may be from 1 to 6, usually 2 to 4, peptide, where the total number of amino acids will be in the range of 1 to 6, usually 2 to 4, where the amino groups will usually be small, e.g. G and A, or hydrophilic, e.g. S, T, N, Q, D, E, K and R, sugars, where the total number of saccharidic groups will generally be in the range of 1 to 6, usually 2 to 4, or combinations thereof, including 1 or more nucleosides which are not involved in hybridizing.

Instead of having a hairpin or stem and loop, one may have a bulge which preferably includes the photoactivatable group in an unreactive environment. The bulge may be as a result of a hairpin or the addition of an additional sequence partially homologous to the side chain. For example, the sequence causing the bulge would lack the passive reactive moiety, as well as the bases complementary to the bases adjacent to the photoactivatable group. The bulge causing sequence would have bases complementary to bases of the side chain distal to the photoactivatable group. In the case of a bulge, the side chain will usually have at least 6, more usually at least 7 bases, where at least two, preferably at least three and not more than about 5 bases, will not be matched by the bulge forming sequence. The bases in the bulge may or may not be matched to provide a sidechain hairpin, the bases usually being other than thymidine. So long as the bulge forming sequence is bound to the side chain, the photoactivatable group will be hindered from reacting with the reciprocal side chain.

Figure 5:
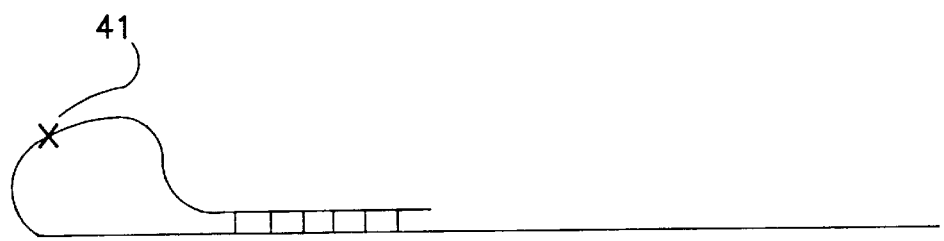
FIGS. 5 and 6 are diagrammatic views of protective embodiments of this invention.

Alternatively, one or both of the stems may be extended by an oligonucleotide of from about 2, usually at least 3 to 10, usually not more than about 8 nucleotides, whose sequence is complementary to a portion of the target complementary portion of the probe sequence. The duplexing portion would be displaced from the junction of the target complementary sequence to the side chain sequence. This is shown in FIG. 5. Again the vertical lines indicate base pairing.

As shown in the figure, the hybridization forms a stem and loop which includes the cross-linking member X 41, particularly the photoactivatable group, so as to create steric hindrance around the portion of the side chain hybridizing with the other side chain. Where both the probes have duplexing at their termini, the hybridizing between the two stems will be substantially diminished. However, when the probe binds to the target or a complementary probe, the side chain portion hybridized to the target homologous sequence of the probe will be displaced by the target or probe, releasing the side chain to hybridize to the other side chain to form the stem. The portion of the probe to which the side chain sequence binds will be selected to bring the side chain around in a stem and loop, the region beginning not more than about 30, usually not more than about 20 nucleotides, from the last nucleotide hybridizing to the target, and beginning at least about 2, usually at least about 4 nucleotides, from the last nucleotide of the side chain hybridizing to the complementary side chain.

Figure 6:
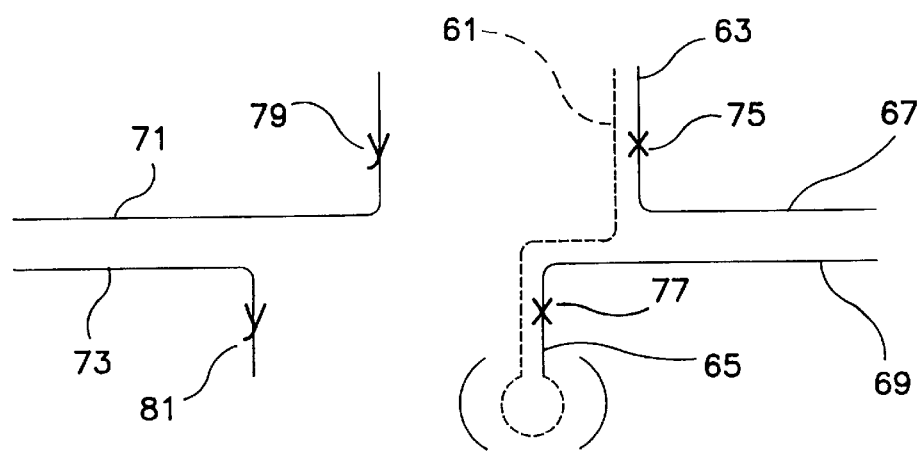

In situations where one has two sets of probes, one may provide for a fifth probe or a side chain extension, (hereafter referred to as the "double side chain duplexing sequence") which serves to hybridize to the side chains on complementary probes. This is exemplified in FIG. 6. For the geometric expansion, the complementary probes as pairs 67 and 69 and 71 and 73, respectively, may be totally or partially overlapping. The double side chain duplexing sequence 61 would hybridize to the two side chains 63 and 65 and the available portions of the target complementary sequence 69. The photoreactive or passive groups X, 75 and 77, are shielded, while the passive or photoreactive groups(in relation to the nature of X) 79 and 81, need not be shielded. The double side chain duplexing sequence may include bases which hybridize with portions of the probe complementary to the target sequence. The portions will usually not exceed five nucleotides, more usually not exceed four nucleotides, where the double side chain duplexing sequence will displace a portion of the sequence homologous to the target. Usually, the double side chain duplexing sequence would have at least about 6 members, more usually at least about 7 members and may have up to 30 members or more, where there will be complementarity between at least 4 members and the side chains, usually at least 5 members and the side chains, preferably there being at least complementarity between the double side chain duplexing sequence and at least 6 nucleotides of the side chains.

There are extensive methodologies for providing cross-linking upon spacial proximity between the side chains of the two probes, to form a covalent bond between one member of the stem and the other member of the stem. Conditions for activation may include photonic, thermal and chemical, although photonic is the primary method, but may be used in combination with the other methods of activation. Therefore, photonic activation will be primarily discussed as the method of choice, but for completeness, alternative methods will be briefly mentioned. In addition to the techniques used to reduce hybridization between the side chains when not bound to the target or complementary probe, conditions may also be employed to provide for a substantial difference in the reaction rate when bound to a template sequence as compared to free in solution. This can be achieved in a wide variety of ways. One can provide concentrations where events in solution are unlikely and activation of the cross-linking group will be sufficiently short lived, so that the activated group is not likely to encounter another probe in solution. This can be tested using control solutions having known concentrations of probes and determining the formation of cross-linked probes in the presence and absence of template. One may use quenchers that act to deactivate cross-linking groups on probes that are free in solution, where the quencher may accept energy, provide a ligand to replace a lost ligand, react with the cross-linking group to inhibit cross-linking with another probe, and the like. By adjusting the amount of quencher in the medium, one can optimize the desired reaction as compared to the background reaction. One may use sensitizers, where reaction only occurs upon activation of the cross-linking moiety by transfer of energy from the sensitizer to the cross-linking moiety. The significant point is that the sensitizer, which will be bound to the probe carrying the passive reactive moiety, is directly irradiated and the energy will be dissipated in solution in the absence of the photoactivatable cross-linking moiety accepting the energy. Acceptance of the energy has a much greater probability when the side chains are involved in stem formation. Sensitizers which may be employed include biphenyl, fluorenone, biacetyl, acetonaphthone, anthraquinone, bibenzoyl, and benzophenone, or other sensitizers, which because of their triplet energies, find particular application with the coumarin functionality. These sensitizers may be joined to the side chain in the same manner as the photo-activatable moiety, as an appropriate site, usually within one or two bases from the passive reactive moiety.

One can also provide for a substantial difference (between probes bound to a template sequence and probes free in solution) in the reaction rate of the members of the cross-linking system by separating the cross-linking member or activatable member from the sequence providing for non-covalent association in one of the two side chains of the probes. In this manner, when the probes are free in solution, although the side chain sequences may be non-covalently associated, upon activation cross-linking will not occur because the requisite proximity of the cross-linking members of the two side chains will not be present. In contrast, when the probes are bound to a template sequence, e.g. the target sequence, the sequences of the side chains will be non-covalently associated and the members of the cross-linking system will also be in the requisite spacial proximity for activation. The cross-linking member will be separated from the sequence in the side chain responsible for non-covalent association with the side chain of the second probe by a sufficient distance so that when the two probes are hybridized to the template sequence, non-covalent association between the side chain sequences may still occur while the activatable members of each side chain will be in sufficient proximity for activation. Using probes with nucleic acid side chains as exemplary, the separation distance between the sequences responsible for non-covalent association and the cross-linking member of the side chain in the first probe may range from 5 to 50 nt, usually from 6 to 40 nt and more usually from 6 to 30 nt.

In one aspect, one can employ photochemistry where a single reactive species on one chain reacts with a group present on the second chain. A large number of functionalities are photochemically active and can form a covalent bond with almost any organic moiety. These groups include carbenes, nitrenes, ketenes, free radicals, etc. One can provide for a donor molecule in the bulk solution, so that probes which are not bound to a template will react with the terminating molecule to avoid cross-linking between probes. Carbenes can be obtained from diazo compounds, such as diazonium salts, sulfonylhydrazone salts, or diaziranes. Ketenes are available from diazoketones or quinone diazides. Nitrenes are available from aryl azides, acyl azides, and azido compounds. For further information concerning photolytic generation of an unshared pair of electrons, see A. Schonberg, Preparative Organic Photochemistry, Springer-Verlag, N.Y. 1968. Illustrative compounds and terminating molecules include olefins or compounds with a labile proton, e.g. alcohols, amines, etc.

For specificity, one may use a molecule which upon photoactivation forms a covalent bond with a specific other molecule or small group of molecules via cycloaddition or photosubstitution reaction. There are a significant number of compounds which will react with nucleic acid bases to form covalent bonds. Thymidine will react with thymidine to form a covalent link. Preferably, other compounds will be used which react with nucleic acid bases. These compounds will include functional moieties, such as coumarin, as present in substituted coumarins, furocoumarin, isocoumarin, bis-coumarin, psoralen, etc., quinones, pyrones, α,β-unsaturated acids, acid derivatives, e.g. esters, ketones, and nitriles; azido, etc.

Instead of having a reaction with a nucleotide, one can provide for two different reactants, where reaction is unlikely when the two reactants are not in proximity upon activation. Reactions of this nature include the Diels-Alder reaction, particularly a photoactivated Diels-Alder cyclization reaction, where a diene, and a dienophile e.g., olefin or acetylene, are employed. Reactive dienes may be employed, such as 1,4-diphenylbutadiene, 1,4-dimethylcyclohexadiene, cyclopentadiene, 1,1-dimethylcyclopentadiene, butadiene, furan, etc. Dienophiles include maleimide, indene, phenanthrene, acrylamide, styrene, quinone, etc. One may provide for sensitized activation to provide for the cyclization, using such photoactivators as benzophenones with cyclopentadiene, which may react with another cyclopentadiene molecule, or a different dienophile. Alternatively, one may employ addition of ketones to olefins, as in the case of benzophenone and isobutylene or 2-cyclohexenone.

Another class of photoactive reactants are organometallic compounds based on any of the d- or f-block transition metals. Photoexcitation induces the loss of a ligand from the metal to provide a vacant site available for substitution. Placement of the organometallic compound on one side chain and a suitable ligand, on the other chain provides a system which relies on the proximity of the two chains for the cross-linking to occur. Suitable ligands may be the nucleotide itself or other moieties, such as amines, phosphines, isonitriles, alcohols, acids, carbon monoxide, nitrile, etc. For further information regarding the photosubstitution of organometallic compounds, see "Organometallic Photochemistry," G. L. Geoffrey, M. S. Wrighton, Academic Press, San Francisco, Calif., 1979.

By using organometallic compounds having stable coordination complexes, where the ligands can be replaced with other ligands upon photo- or thermal activation, one can provide for stable cross-linking. Examples of organometallic compounds which may serve as cross-linking agents include four coordinate Group VIII metals, particularly noble metals, cyclopentadienyl metal complexes, having at least one other ligand, and the like.

One may also employ active monomers which can dimerize with a second monomer, such as styrene, acrylonitrile, vinyl acetate, acenaphthylene, anthracene, etc. By activating one of the monomers photolytically, the activated monomer can react with the other monomer on the other side chain. Particularly, by using two different monomers, where the second monomer provides for a more stable active species than the first monomer, one may include a quencher in the reaction medium so as to quench the active intermediate. In some instances, the intermediate will self-quench by elimination or other suitable reaction. One may also provide for photolytically activated homolytic or heterolytic cleavage, such as active halides, e.g. benzyl halides, particularly bromo and iodo, where upon cleavage, the active molecule would act with a recipient molecule, such as an olefin which would provide for addition of the carbon and halogen across the double bond.

Other reactions which might be employed include photonucleophilic aromatic substitution.

Thermal activation may also be employed, but is less desirable in many cases since until the temperature is lowered, the reactive species is maintained. Therefore, this will usually require lower concentrations of at least one of the probes, the ability to rapidly change the temperature of the system, and the selection of reactants which provide for a high energy barrier for reaction in the absence of spacial proximity. Reactions which may be employed include ones described above for photolytic activation, such as metal coordination complex cross-linking, and the like. Illustrative of such cross-linking is the use of platinum tetradentate complexes, e.g. ammonia complexes.

Also, chemical reactions can be employed where one provides for cycling of the active moiety in the absence of reaction with the recipient reactant. Thus, one can provide for a redox couple, such as ferrous and ferric ions, where the active species free in solution would normally be inactivated prior to encountering the recipient compound. For example, one could have a hydroperoxide as the reactant species and an active olefin as the recipient. Upon reduction of the hydroperoxide, a free radical can be obtained which can react with the electron donor compound, which can then be further reduced to a stable compound.

Any of the various groups indicated may be modified by replacement of a hydrogen with a functionality or convenient linking group for attachment to the backbone of the side chain. These functionalities will, for the most part, be oxy, oxo, amino, thio, and silyl.

The probe homologous sequence which binds to the template will usually be naturally occurring nucleotides, but in some instances the phosphate-sugar chain may be modified, by using unnatural sugars, by substituting oxygens of the phosphate with sulphur, carbon, nitrogen, or the like, by modification of the bases, or absence of a base, or other modification which can provide for synthetic advantages, stability under the conditions of the assay, resistance to enzymatic degradation, etc. The homologous sequence will usually have fewer than 10 number % of the nucleotides different from the target sequence, and usually the lesser of 10 number % and 10 nucleotides, more usually 5 nucleotides. The relationship of the pairs of probes will usually come within the same limitations, but will more usually be complementary, that is, have perfect nucleotide pairing. Differences between sequences may include insertions, deletions, and substitutions, i.e. transitions and transversions. If one wishes one may have more than one set of a pair of probes specific for a target sequence, and may simultaneously have 2 or more sets of probes, usually not more than 10 different sets, more usually not more than about 5 different sets, directed to different target sequences. A probe set is one pair for linear expansion and two pairs of probes, for geometric expansion, where for geometric expansion, the probes have homologous binding sequences, so as to bind to target sequence and to each other. Where one has a plurality of probe sets, each of the probe sets will generally be distinguishable in some assay, for example, by size difference, by label difference, by sequence, etc.

In some instances it may be desirable to provide three different probes, where three probes define three contiguous sequences and two stems, the middle probe having two side chains, so as to interact with each of the other side chains of the other two probes. This can be particularly useful with regions of polymorphism, where the central probe is directed to a conserved region, and one or both of the other probes are directed to polymorphic regions or vice versa. One may then use a plurality of probes, one for each of the polymorphic regions, where cross-linking will result for any of the polymorphic sequences being present.

The probes may be prepared by any convenient synthetic scheme. In one scheme, the side chains may be prepared first, followed by being linked to the sequence homologous to the target sequence. The synthesis of the side chains will depend, of course, on the nature of the pairing groups. For oligonucleotides, conventional manual or automated techniques may be employed. One or more of the monomers may comprise a cross-linking group. By employing a linker in the backbone which employs a deoxyribosylphosphate group or can substitute for the deoxyribosylphosphate group, the cross-linking containing group may be readily inserted into the backbone during the synthesis. The side chains may have terminal functionalities that allow for direct linkage of the sequence homologous to the target sequence, e.g. a nucleotide 5'-triphosphate or nucleotide having a free 3'-hydroxyl. The homologous sequence may be joined by ligation, by using the side chains in conjunction with a primer for PCR, or other linking means. The side chains may be used to terminate a chain being produced on a bead or may be the initiating group bound to the bead by a cleavable linker. Thus side chains can be provided as reagents for use in automated synthesis, where the side chains will provide the initiating or terminating reagent. Various attachment groups may be provided for the side chain, where the side chain is to be attached to a bead. Functionalities on the bead can be hydroxy, carboxy, iminohalide, amino thio, active halogen or pseudohalogen, carbonyl, silyl, etc. For ease of removal from the bead, various linkers may be employed which will include groups, such as benzhydryl ethers, acetals, including sulfur analogs thereof, o-nitrobenzyl ether, 7-nitroindanyl, cyclic anhydrides, polypeptides having a sequence recognized by a peptidase, silanyl, β-(electron withdrawing group) substituted esters, or the like. The particular linking group which is selected will depend upon the nature of cross-linking group and the manner in which it is bonded to the side chain backbone.

Of particular interest are compositions which provide the hybridizing side chains and can be joined to sequences homologous to target sequences, to provide probes. Combinations of stem forming oligonucleotides are used. Depending on which technique is used to diminish probe cross-linking background, the compositions providing for a cross-linking member will have the following formula:

$$N\text{-}X_a\text{-}Z\text{-}X_b\text{-}Z_c\text{-}(X_a)_c \quad (1)$$

$$N\text{-}A\text{-}Z\text{-}B\text{-}X_a, \text{ or} \quad (2)$$

$$N\text{-}X^1_a\text{-}Z\text{-}X^2_b\text{-}A\text{-}X^3 \quad (3)$$

wherein:

N is a moiety capable of ligation to a nucleotide, which may comprise an hydroxyl group, a phosphate group, a triphosphate group, or the like, including nucleosides, nucleotides, phosphoramidites, phosphate esters, sugars, hydroxyalkyl or -aryl groups, and the like;

X is a nucleotide, naturally occurring or synthetic, capable of hydrogen bonding to another nucleotide, preferably at least one X will be adenosine, and when other than duplex formation of the stem is present in the probe, usually at least about 50% of the stem base pairing X's will be adenosine; when Z reacts with thymidine, generally of the total nucleotides in the stems, at least about 30%, more usually at least about 50% will be thymidine and adenosine, where the hybridizing nucleotides have each stem in the same direction, e.g. 5'-3' or 3'-5 or opposite direction, e.g. 5'-3' pairing with 3'-5'; the combination of (1) and (1) and (1) and (3) will have the stem oligonucleotides in the opposite direction, while the combination of (1) and (2) will have the stem oligonucleotides in the same direction;

Z is a cross-linking group having, usually as a side chain, a moiety capable of cross-linking with another moiety, conveniently with a nucleotide, or a member of complementary specific reactive pair, more particularly as a result of photoactivation (see groups described above); or a sensitizer (see groups described above), at least one Z in a combination of stems will be a cross-linking moiety; Z will usually be of at least about 8 atoms other than hydrogen, more usually at least about 10 atoms other than hydrogen, and not more than about 50 atoms, more usually not more than about 36 atoms other than hydrogen, where Z may be aliphatic, alicyclic, aromatic, heterocyclic, or combinations thereof, where cyclic having from about 1 to 3 rings, which may be fused or non-fused, composed of carbon, oxygen, nitrogen, sulfur and phosphorus, comprising functional groups, such as oxy, oxo, amino, thio, cyano, nitro, halo, etc., usually having at least one heteroatom, more usually at least about 3 heteroatoms, and not more than about 10 heteroatoms;

$X^1$ and $X^2$ are a nucleotide or oligonucleotide of the stems which hybridize with each other and will generally be at least 2 nucleotides, having a total number of nucleotides in the range of about 2 to 20, usually 2 to 18, more usually about 3 to 16, and preferably not more than about 8 hybridizing base pairs, more usually not more than about 6 hybridizing base pairs, usually in the range of about 2 to 6, more usually in the range of 3 to 6, hybridizing base pairs;

$X^3$ is a sequence of at least 2, usually at least 3, nucleotides which is complementary to and hybridizes with a sequence of the probe which binds to the target sequence, so as to form a hairpin comprising at least 3 members, usually at least about 4 members and not more than about 12 members, usually not more than about 8 members which are not involved in base pairing, and which hairpin includes Z, where Z will be a cross-linking member which does not react with the base of a nucleoside;

A and B are linking groups, which will usually be other than nucleotides, where A and B are of sufficient length to permit the two stems to hybridize with each stem in the same direction, e.g. 5'-3' or 3'-5', so that the number of atoms in A and B will be determined by the length of the complementary stem, the nature and flexibility of A and B, and the like; usually A and B will have a total of at least about 10 atoms in the chain, more usually at least about 12 atoms in the chain and not more than about 60 atoms in the chain, where the side groups will be selected for synthetic convenience, solubility, inertness, absence of interference in the assay and the like; A and B may be aliphatic, alicyclic, aromatic, heterocyclic or combinations thereof, and may be monomeric or oligomeric, such as polyethers, e.g. polyalkyleneoxy, oligopeptides, e.g. polyglycyl, polyurethanes, polymethylene, e.g. polyethylene, polyacrylate, polyvinylether, etc., ; usually A and B will be at least about 6 carbon atoms, more usually at least about 8 carbon atoms and not more than about 100 carbon atoms, more usually not more than about 60 carbon atoms and preferably not more than 36 carbon atoms, usually having at least 1 heteroatoms, more usually at least 2 heteroatoms and not more than about 36 heteroatoms, usually not more than about 20 heteroatoms, where the heteroatoms may be oxygen, nitrogen, sulfur, phosphorus, halogen, and the like; and a, b and c are integers of a total in the range of 2 to 20, where a is at least one, b may be 0 or greater, usually at least 1, c usually being 0 or 1, and the total number of nucleotides for base pairing are at least 2, usually at least 3 and not more than about 20, usually not more than about 16, preferably not more than about 8, generally being in the range of 4 to 6 base pairs.

The side chain compositions described above are used in combination for linking two adjacent sequences homologous to the target sequence. Either of the side chain compositions can be selected for linking to the 3' or 5' terminus of the homologous sequence. The second side chain will usually have nucleotides complementary to the nucleotides of the first chain to provide hydrogen bonding. In the simplest second chain, it may be a poly-T, where the cross-linking group reacts with thymidine, and the nucleotides in the first chain are adenosine. Where the first chain has other than adenosine bases, the second chain will usually have the complementary bases. The first and second side chains can be provided as reagents for linking to the homologous sequences, as termini of primers for PCR to provide the probes directly, or the like.

In addition, one or both of the side chain compositions may terminate with a label (including ligand) which allows for detection, such as a directly detectable label, e.g. radiolabel or fluorescer; chemiluminescer, biotin, antigen, photocatalyst, redox catalyst, or the like, for detection of the cross-linked probes.

In carrying out the assay, the sample may be subjected to prior treatment. The sample may be a cellular lysate, isolated episomal element, e.g. YAC, plasmid, etc., virus, purified chromosomal fragments, cDNA generated by reverse transcriptase, mRNA, etc. Depending upon the source, the nucleic acid may be freed of cellular debris, proteins, DNA, if RNA is of interest, RNA, if DNA is of interest, size selected, gel electrophoresed, restriction enzyme digested, sheared, fragmented by alkaline hydrolysis, or the like.

For linear expansion, only one pair of probes is required. After each melting step, linked probes will be obtained in proportion to the amount of target DNA present. For geometric expansion, two pairs of probes will be used. Where the target sequence is a single strand, the initial pair would be homologous to the target and the pair having the analogous sequence to the target added concomitantly or after the first cycle of cross-linking. Where the sample is double stranded, then both pairs of probes, a pair for each strand, are added initially.

The probes and template will be brought together in an appropriate medium and under conditions which provide for the desired stringency to provide an assay medium. Therefore, usually buffered solutions will be employed, employing salts, such as citrate, sodium chloride, tris, EDTA, EGTA, magnesium chloride, etc. See, for example, Molecular Cloning: A Laboratory Manual, eds. Sambrook et al., Cold Spring Harbor Laboratory, Cold Spring Harbor, N.Y., 1988, for a list of various buffers and conditions, which is not an exhaustive list. Solvents may be water, formamide, DMF, DMSO, HMP, alkanols, and the like, individually or in combination, usually aqueous solvents. Temperatures may range from ambient to elevated temperatures, usually not exceeding about 100° C., more usually not exceeding about 90° C. Usually, the temperature for photochemical and chemical cross-linking will be in the range of about 20 to 60° C. For thermal cross-linking, the temperature will usually be in the range of about 70 to 120° C.

The ratio of probe to target nucleic acid in the assay medium may be varied widely, depending upon the nature of the cross-linking agent, the length of the homology between the probe and the target, the differences in the nucleotides between the target and the probe, the proportion of the target nucleic acid to total nucleic acid, the desired amount of amplification, or the like. The probes will usually be about at least equimolar to the target and usually in substantial excess. Generally, the probes will be in at least 10 fold excess, and may be in $10^6$ fold excess, usually not more than about $10^{12}$ fold excess, more usually not more than about $10^9$ fold excess in relation to the target during the first stage. The initial ratio of probes to target nucleic acid may be maintained during successive cycles or may be allowed to diminish by the amount of reaction of the reactive species. The ratio of one probe to the other may also be varied widely, depending upon the nature of the probes, the differences in length of the homologous sequences, the binding affinity of the homologous sequences to the target sequence, the role of the probe in the cross-linking system, and the like. Conveniently, the probes may be equimolar, but may vary in the range of 1:1–20 more frequently, 1:1–10, where, when there is only one reactive or activated species, the passive side chain will usually be in excess to substantially ensure that the passive probe is bound to the template whenever the photoreactive probe is present on the template.

Where the sample is double stranded, it will usually be denatured, where denaturation can be achieved chemically or thermally. Chemical denaturation may employ sodium hydroxide in an appropriate buffered medium, e.g., tris-EDTA (TE). Triplex formation may be employed. However, where triplex formation requires complexing the probes with RecA, there will generally be no advantage to such a protocol, since it requires the continuous presence of natural or active RecA which will be subject to denaturation.

During the course of the reaction, depending upon how the assay is carried out, there may be significant evaporation. Therefore, it will normally be desirable to put a coating over the assay medium which inhibits evaporation. Various heavy oils may find use, such as mineral oil, silicone oil, vegetable oil, or the like. Desirably, the oil should be free of any contaminants which might interfere with the assay. Alternatively, one may use sealed systems, where evaporation is inhibited.

The amount of target nucleic acid in the assay medium will generally range from about 0.1 yuctomol to about 100 pmol, more usually 1 yuctomol to 10 pmol. The concentration of sample nucleic acid will vary widely depending on the nature of the sample. Concentrations of sample nucleic acid may vary from about 0.01 fM to 1 $\mu$M. In fact, the subject method has the capability to detect a single molecule in the absence of significant interference. The amount of the probes may be varied and their concentration varied even more widely, in that there will usually be at least about an equimolar amount of the probes and as indicated previously, large excesses of one or the other or both of the probes may be present. Where the target is single stranded, one may initially use substantially less of the probe in relation to the target since there is no competition between the probes and an homologous sequence for the target. Where the target is double stranded, initially, one will normally use more of the probes so as to enhance the competitive advantage of the probes for the complementary sequences as against the target sequences of the sample.

Where chemical denaturation has occurred, normally the medium will be neutralized to allow for hybridization. Various media can be employed for neutralization, particularly using mild acids and buffers, such as acetic acid, citrate, etc., conveniently in the presence of a small amount of an innocuous protein, e.g. serum albumin, β-globulin, etc., generally added to provide a concentration in the range of about 0.5 to 2.5%. The particular neutralization buffer employed is selected to provide the desired stringency for the base pairing during the subsequent incubation. Conveniently the stringency will employ about 1–10×SSC or its equivalent. The base pairing may occur at elevated temperature, generally ranging from about 20 to 65° C., more usually from about 25 to 60° C. The incubation time may be varied widely, depending upon the nature of the sample in the probes, generally being at least about 5 minutes and not more than 6 hours, more usually at least about 10 minutes and not more than 2 hours.

After sufficient time for the base pairing to occur, the reactant may be activated to provide cross-linking. The activation may involve light, heat, chemical reagent, or the like, and will occur through actuation of an activator, e.g. a means for introducing a chemical agent into the medium, a means for modulating the temperature of the medium, a means for irradiating the medium and the like. Where the activatable group is a photoactivatable group, the activator will be an irradiation means where the particular wavelength which is employed may vary from about 250 to 650 nm, more usually from about 300to 450 nm. The intensity will depend upon the particular reaction and may vary in the range of about 0.5 W to 250 W.

In order to obtain amplification, it will now be necessary to melt probes bound to the template. Melting can be achieved most conveniently by heat, generally heating to at least about 60° C. and not more than about 100° C., generally in the range of about 65°0 C. to 95° C. for a short period of time, frequently less than about 5 minutes, usually less than about 2 minutes, and normally for at least about 0.1 minute, more usually for at least about 0.5 minute. While chemical melting may be employed, it is inefficient and will only be used in special circumstances, e.g. thermal activation. After the melting, the medium will usually be cooled by at least about 20° C., usually 30° C. or more. During the incubation and photoactivation, the temperature will be dropped to below 65° C., usually below about 55° C. and may be as low as 15° C., usually be at least about 40° C.

Activation may then be initiated immediately, or after a short incubation period, usually less than 1 hour, more usually less than 0.5 hour. With photoactivation, usually extended periods of time will be involved with the activation, where incubation is also concurrent. The photoactivation time will usually be at least about 1 minute and not more than about 2 hours, more usually at least about 5 minutes and not more than about 1 hour. This process may be repeated if desired, so that the melting-annealing and photoactivation may occur with from 1 to 40 cycles, more usually from 1 to 30 cycles, preferably from 1 to 25 cycles. During the cycles, the amount of probe may be replenished or enhanced as one proceeds. The enhancement will usually not exceed about five fold, more usually not exceed about two fold.

As the reaction proceeds, in the case of linear expansion, at each stage there will be hybridization with the target and additional linked probes formed in relation to the amount of target DNA. For geometric expansion, if the original target was single stranded, in the first cross-linking step, there will be the target nucleic acid as a template and the cross-linked nucleic acid, which can now serve as a template for the probes having the same sequence as the target nucleic acid. In the next stage, one will now produce templates of probes having the same sequence as the target and the homologous sequence as the target. Thereafter, for each subsequent cycle, one will form cross-linked probes on the target sequence template, as well as on the two different cross-linked probe templates. The situation is analogous with double stranded nucleic acid, except that in the first step one needs to provide probes for both target templates and there is an initial geometrical expansion as to both of these probe sequences.

The resulting compositions will comprise cross-linked probes. Such compositions may be used as probes to identify homologous sequences, to isolate target sequences having homologous sequences, and the like. The compositions find particular use in identifying the presence of the target sequence in the sample.

At the end of the iterations or cycles of steps, the presence and amount of cross-linked probes may be determined in a variety of ways. Conveniently, gel electrophoresis may be employed and the amount of cross-linked probes determined by the presence of a radioactive label on one of the probes using autoradiography; by staining the nucleic acid and detecting the amount of dye which binds to the cross-linked probes; by employing an antibody specific for the dimerized probe, particularly the cross-linked area, so that an immunoassay may be employed; or the like.

If desired, for quantitation, an internal control may be provided, where a known amount of a known sequence is introduced, with a known amount of probes, equivalent to the probes for the target sequence of interest. By carrying out the assay, one would obtain linked probes from the control and linked probes related to any target sequence present in the sample. By taking aliquots of the assay medium during the assay and after each or different numbers of cycles, one can determine the efficiency of the assay conditions, as well as ratios of cross-linked control probes to cross-linked sample probes. If one has an estimate of the amount of sample DNA which should be present, one can terminate the assay once the amount of cross-linked control probe indicates that there should be sufficient cross-linked sample probe to be detectable. By having a fluorescent molecule on one side chain and a quencher molecule on the other side chain, one can monitor the degree of cross-linking in relation to the change in fluorescence of the assay medium.

Instead of separating the probes from the assay medium, detection techniques can be employed which allow for detection during the course of the assay. For example, each of the probes may be labeled with different fluorophores, where the energy of the emitted light of one of the fluorophores is in the absorption band of the other fluorophore. In this way, there is only energy transfer when the two fluorophores are in close proximity. See, for example, U.S. Pat. Nos. 4,174,384, 4,199,599 and 4,261,968. By exciting a first fluorophore at a wavelength which does not excite the second fluorophore, where the first fluorophore emits at a wavelength absorbed by the second fluorophore, one can obtain a large Stokes shift. One reads the fluorescence of the second fluorophore, which is related to the number of first and second fluorophores which are in propinquity. During the course of the assay, at the end of each cycle, one can determine the fluorescence of the medium at the emission wavelength of the second fluorophore as a measure of the amount of cross-linking and indicative of the presence of the target sequence and its amount. To provide a more quantitative measurement, one can use controls having a known amount of target sequence and compare the fluorescent signals observed with the sample and control.

By virtue of the fact that one is linking two probes, one can use different labels on the different probes to allow for detection of cross-linking. Since the two labels will not be held together except when the two probes are cross-linked, one can use the existence of the two labels in a single molecule to measure the cross-linking. For example, by having one label which is a member of a specific binding pair, e.g. antibody and ligand, such as digoxigenin and anti-digoxigenin, biotin and streptavidin, sugars and lectins, etc., and having the other label providing a detectable signal either directly or indirectly, one has the opportunity to separate the cross-linked probes on a solid support, e.g. container surface or bead, e.g. magnetic bead, where the detectable label becomes bound to the solid support only when part of the cross-linked probes. For direct detection, one may have fluorophores, chemiluminescers, radiolabels, and the like. For indirect detection, one will usually have a ligand which binds to a reciprocal member, which in turn is labeled with a detectable label. The detectable label may be any of the above labels, as well as an enzyme, where by adding substrate, one can determine the presence of cross-linked probe.

Where one has ternary probes, particularly with a polymorphic target, a central probe to a conserved region and outer probes for the polymorphic regions, one can use differentially detectable labels on the outer probes and a ligand on the central probe for separation. In this way, one can readily determine which polymorphism(s) are present. The separation of the cross-linked probes provides the advantage of isolation of the cross-linked probe from the uncross-linked probe carrying the label, allows for washing of the bound probe, and removal of non-specifically bound label. Thus, background due to uncross-linked label can be diminished.

A diverse range of target sequences can be determined in accordance with the subject protocols. The subject methodology may be used for the detection of bacterial and viral diseases, plasmid encoded antibiotic resistance markers, genetic diseases and genetic testing, veterinary infections for commercial livestock and pets, fish stocks in fish farming, sexing of animals, analysis of water systems for contamination by organisms or waste materials, and the like.

Among bacterial and viral diseases are: *Chlamydia trachomatis, Neisseria gonorrhoeae, Mycobacterium tuberculosis, Haemeophilus ducreyi* (chancre, chancroid), *Treponema pallidium* (syphilis), *Helicobacter pylori,* Mycoplasma, *Pneumocystic carinii, Borrelia burgdorferi* (Lyme disease), Salmonella, Legionella, *Listeria monocytogenes,* HIV I and II, HTLV-II, Hepatitis A, B, C, and D, Cytomegalovirus, human Papillomavirus, Respiratory syncytial virus, Epstein-Barr virus, Dengue (RNA virus), Eastern and Western Encephalitis virus (RNA viruses), Ebola virus, and Lassa virus.

Chlamyida trachomatis is the cause of the most prevalent sexually transmitted disease in the U.S., leasing to 4 million cases annually. Nucleic acid targets useful for detecting all 15 serovars of C. trachomatis include: 16S ribosomal RNA gene and the rRNA itself, and the major outer membrane protein (MOMP) gene. C. trachomatis also contains a highly conserved 7.5 kb cryptic plasmid. Allserovars contain this plasmid and there are typically 7–10 copies of the plasmid per elementary body.

Neisseria gonorrhoeae, the cause of gonorrhoeae, has species specific sequences useful for its detection, which include: 16S ribosomal RNA gene and the rRNA itself; a 4.2 kb cryptic plasmid that is present in 96% of al clinical isolates with approximately 30 copies present in each bacterium; and the cppB gene, typically present on the plasmid, is present in all strains, including those lacking the plasmid.

Mycobacterium tuberculosis, the cause of tuberculosis, has species specific nucleic acid sequences useful for detection, which include: 16S ribosomal RNA gene and the rRNA itself; and an insertion sequence, IS6110, specific for the M. tuberculosis complex, which comprises M. tuberculosis, M. africanum and M. microti. The copy number of the insertion sequence varies from 1–5 copies in M. bovis to 10–20 copies in M. tuberculosis.

Salmonella has species specific genes which include: an insertion sequence IS200; invAgene, himA gene; and the Salmonella origin of replication, ori. The invAgene has been identified in 99.4% of about 500 strains of Salmonella tested. This gene codes for proteins essential for invasion by the Salmonella organism into epithelial cells. In addition, 142 strains from 21 genera of bacteria different from Salmonella were al found to lack the invA gene. Similarly, the insertion sequence IS200 has been identified in almost all Salmonella strains. One additional advantage in targeting the IS200 sequence is the presence of multiple gene copies in most strains of Salmonella.

Hepatitis B virus is a DNA virus with an unusual genomic organization. Virions are likely to be detected in the blood. There is a high degree of conservation in many regions of the genome. The genome is small, 3.2 kb, and, with overlapping reading frames, there is strong selection pressure against sequence variation. Candidate probes from the overlap between the polymerase and S antigen coding regions include: GTTTYCTTGTTGAACAAAAATCCT (SEQ ID NO:01) and TITCTAGGGGGAACACCCGTGTGTCT (SEQ ID NO:02), where the probe would include at least about 12 nt coming within the indicated sequences.

Hepatitis delta is a single-stranded RNA genome that is encapsulated in Hepatitis B virus coat proteins. Delta infection requires simultaneous or pre-existing HBV infection and generally aggravates the clinical condition. Virions containing either the delta or HBV genome may be detected in blood samples. The delta genome encodes one known protein, the delta antigen, that is believed to be required for replicating the viral RNA genome (cellular constituents are also required). Sequences of interest as probes come within the sequence:

CTGGGAAACATCAAAGGAATTCTCG-GAAAGAAAGCCAGCAGTCTCCTCTT TACA-GAAAAG (SEQ ID NO:03).

Cytomegalovirus has a large linear double-stranded DNA genome. The virus is found in blood and to a limited extent infects lymphocytes and is also found in urine. There are repeated regions in the genome allowing for detection of such repeated regions. Where only limited viral transcription has occurred, the Immediate Early Region would be the target, while for productive infection, probes to the viral glycoprotein genes would be employed.

Human papillomavirus is a circular double-stranded DNA and probes may be targeted to any region of the genome. Of particular interest are probes to the E6/E7 coding region, where one may discriminate between genotypes, e.g. HPV 16 and 18, of interest in North America, while other genotypes, such as 31, 33, 35, 51, and 53 may be diagnostic for cervical cancer in other parts of the world.

Epstein-Barr virus, the causative agent of mononucleosis and lymphocytic cancers, may be assayed in the sputum.

For acute viral infections, such as Ebola and Lassa, a rapid test not dependent on antibody formation could be of advantage in treating the patient. CSF fluids may be monitored for bacterial and viral infections, resulting in meningitis and encephalitis. Transplant patients may be monitored for CMV, herpes, BK and JC viruses.

In the case of plasmid-encoded antibiotic resistance genes, there is great concern whether a pathogenic organism is resistant to one or more antibiotics. Vancomycin is an extremely important drug for treatment of strains of Staphylococcus and Streptococcus that are resistant to other antibiotics. Some strains of enterococcus are resistant to vancomycin. Probing for vancomycin resistance may serve to reduce the transmission of vancomycin resistance. Probes for detecting vancomycin resistance include:

CATAGGGGATACCAGACAATTCAAAC (SEQ ID NO:04);

ACCTGACCGTGCGCCCTTCACAAAG (SEQ ID NO:05);

ACGATGCCGCCATCCTCCTGCAAAA (SEQ ID NO:06; and (SEQ ID NO:07).

Other targets of interest are the TEM-1 gene (β-lactamase) found in Enterobacteriaceae; TEM-1 gene in penicillinase producing *N. gonorrhoeae* (PPNG) plasmid; genes conferring aminoglycoside antibiotic resistance; genes conferring erythromycin resistance; and genes conferring rifampin resistance, especially associated with *M. tuberculosis*.

Also of interest is amniocentesis or other procedure for isolating fetal DNA, where the interest may be in the sex of the fetus, gross chromosomal aberrations, e.g Down's syndrome, where one would quantitate the level of chromosome 21.

The sequences specific for the various pathogens, genes or the like will provide for specificity as to a particular genus, species, strain, or a particular gene, structural or non-structural. Usually, at least 15, more usually at least 18 nt probes will be employed which are homologous to the target of interest. These homologous sequences are joined to an appropriate side chain to provide the probe. There will be at least one set of probes, usually at least two sets of probes, where the two sets are homologous to complementary strands of the target sequence. Combinations of sets of probes for the pathogens may be provided as kits, where more than one portion of the target host genome may be targeted for binding by the probes. Probes will be selected to provide for minimum false positives, screening the probes with samples from a plurality of individuals from whom one would obtain physiological samples, e.g. blood, serum, urine, spinal fluid, saliva, sweat, hair, or other source of DNA or RNA to be detected.

The samples will be processed in accordance with conventional ways. Where cells are involved, the cells may be lysed chemically or mechanically and the nucleic acid isolated. Where RNA is the target, inhibitors of RNAses will be employed and the RNA will usually be reverse transcribed to provide the target sequence as DNA. Processing may involve fragmentation of the nucleic acid by mechanical means, restriction enzymes, etc. Separations may be involved, where the nucleic acid may be separated by size, e.g. electrophoresis, chromatography, sedimentation, etc. Usually, the nucleic acid will be freed of other components of the lysate, such as membranes, proteins, sugars, etc., frequently being denatured in the process. The particular manner of isolating the target nucleic acid is not critical and will be chosen in accordance with the nature of the sample, the nature of the target, and the like.

For carrying out the methodology, various heating and cooling systems may be employed, such as a thermal cycler, regulated temperature baths, and the like.

The repetitive nature of some of the steps of the methodology, e.g. melting and annealing of nucleotide sequences and activation of the activatable groups of the probes, provides for the opportunity of employing automatic devices for performing the subject assays. Of interest are automatic devices which automate the (1) preincubation, (2) hybridization, (3) photoirradiation, (4) denaturation and (5) post-processing steps of the subject methodology, and which are capable of cycling between steps 2–4. Automatic devices which may be employed will generally comprise a means for controlling the base pairing or hybridization conditions of the assay medium, e.g. for modulating the temperature of the medium; and a means for actuating, in a manner responsive to the conditions of the assay medium, an activator of the activatable groups of the probes.

The means for controlling the base pairing conditions of the assay medium may be any means capable of modulating the conditions of the medium, preferably reversibly, from a first state in which base pairing of complementary nucleotide sequences occurs, i.e. medium conditions conducive to annealing or hybridization of complementary nucleotide sequences, to a second state in which base-paired or hybridized nucleotide sequences dissociate or melt. As described above, the conditions of the assay medium may be modulated through both thermal and chemical means, but thermal means are preferred. Thus, the means may be one which is capable of reversibly modulating these conditions of the assay medium.

Where melting and annealing of complementary nucleotide strands during an assay is accomplished through changes in the thermal conditions of the medium, the means for modulating the base pairing conditions will be one which is capable of changing the temperature of the medium from a first temperature in a range at which base pairing occurs to a second temperature in a range at which annealed nucleotide sequences dissociate. The thermal modulation means should be able to maintain the assay medium at a substantially constant temperature, i.e. within a 1 to 2° C. variation, within the ranges of the first and second temperatures. Furthermore, the thermal modulation means will preferably provide for an adjustable rate of transition between the first and second temperatures. Suitable means for thermal modulation of the assay medium include thermal cyclers, and the like.

Also present in the subject devices will be a means for actuating an activator of the activatable groups of the probes. This actuating means is responsive to assay medium conditions, so that the activator of the cross-linking system, e.g. the source of irradiation in photoactivatable systems, is operative during conditions of base pairing and inoperative during conditions of nucleotide dissociation or melting. Conveniently, this activation means may be a circuit that is configured to be responsive to the assay medium conditions and controls the operation of the activator.

Control circuits which may be employed in the subject devices are circuits configured to actuate an activator, e.g. an irradiation means, at a predetermined assay medium condition or set of assay medium conditions. Suitable control circuits will include a means for transducing the conditions of the assay medium into an electrical signal and a means for triggering the activator in response to the transduced electrical signal. Illustrative control circuits which may be employed in the subject devices are provided in FIGS. 1 and 2.

FIG. 1 provides a block diagram of a control circuit where an irradiation source, the activator, is activated when the temperature of the assay medium is below a predetermined temperature or set temperature, e.g. below the temperature at which base pairing of complementary nucleotide sequences occurs. Circuit 10 comprises a thermistor 12 whose resistance varies in response to changes in the temperature of the assay medium with which it is in contact. Circuit 10 also comprises a potentiometer or variable resistor 14, an operational or differential amplifier 16 and a transistor 18 which collectively operate to activate irradiation source 20 via switch or relay 22 when the temperature of the medium is below the set temperature. Circuit 10 also comprises LED 24 which signals that switch 26 is closed, thereby closing the circuit loop.

During operation, the set temperature of the assay medium below which the circuit will actuate the irradiation source is controlled by adjusting potentiometer 14. When the temperature measured by thermistor 12 is above the set temperature, the resistance of the thermistor decreases so that the output of operational amplifier 16 is insufficient to activate the transistor 18. Since the transistor 18 is inactive, current does not flow through relay 28 and light circuit 22 remains in the open position, whereby the irradiation source remains inactive. When the temperature sensed by thermistor drops below the set temperature, the resistance of the thermistor increases to a point at which the output of operational amplifier 16 is sufficient to activate transistor 18. Since the transistor 18 is now activated, current flows through relay 28 and light circuit 22 closes (not shown), whereby the irradiation source is turned on.

Figure 2:
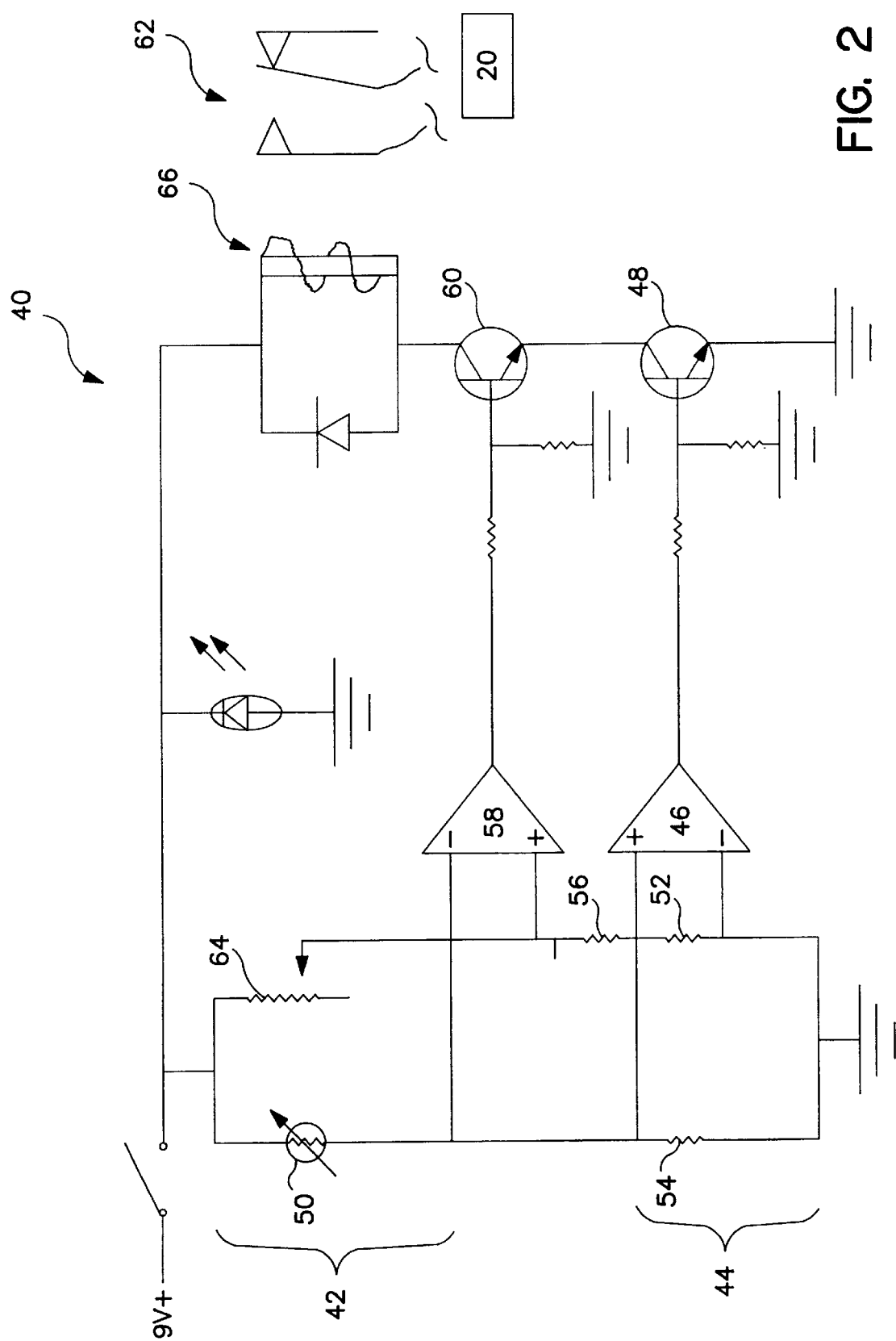
FIG. 2 is a block diagram for a second embodiment of control circuit of an automatic device according to the subject invention.

Instead of having a circuit which is responsive to a single assay medium condition, e.g. a single temperature, circuits responsive to a set of assay medium conditions, such as two temperatures, may be successfully employed. FIG. 2 provides a block diagram of a second control circuit wherein the irradiation source is only activated when the temperature of the assay medium is within a narrow, predetermined temperature range, e.g. between 40 and 43° C. In other words, the irradiation source is activated when the temperature of the assay medium is: (a) below a first predetermined or set temperature and (b) above a second predetermined or set temperature. In FIG. 2, circuit 40 comprises a first loop 42 which is analogous to circuit 10 in FIG. 1 and a second loop 44 which is parallel with first loop 42, where second loop 44 comprises a second operational amplifier 46 and transistor 48. As in the circuit depicted in FIG. 1, the output of operational amplifier 58 is only sufficient to activate transistor 60 and thereby close light circuit 62 via activation of switch 66 when the temperature of the assay medium sensed by thermistor 50 is below a first set temperature T1. The first set temperature T1 is determined by potentiometer 64. The output of operational amplifier 46 is sufficient to activate transistor 48 only when the temperature of the assay medium, as sensed by thermistor 50, exceeds a set temperature T2, a fixed temperature below T1. T2 is determined by resistors 52, 54 and 56, where the choice of resistance values may be readily determined by calculation depending on the desired set temperature T2. Since both transistors 60 and 48 must be activated for current to flow through relay 66, light circuit 62 will only be closed, thereby activating irradiation source 20, when the temperature of the assay medium as determined by thermistor 50 is between T1 and T2.

Automatic devices according to the subject invention will also comprise an assay containment means for holding the assay medium during the assay. The assay containment means may be any means capable of holding a fixed volume of assay medium, where the containment means will allow for modulation of the base pairing conditions of the medium and activation of the activatable groups by the activator of the device. For example, where a thermal modulation means is employed, the containment means should allow for accurate temperature control of the medium in the containment means, e.g. an eppendorf tube in a thermal cycler. Where activation is accomplished by irradiation, the containment means should allow for irradiation of the sample, where the shape of the containment means may provide for substantially uniform irradiation of the sample, e.g. a container which holds the assay medium in thin, film like layer. The containment means may be any convenient shape, such as a vial, tube, slide, channel, chamber, cylinder and the like.

Automatic devices according to the subject invention comprising means for modulating the base pairing conditions of the assay medium and means for actuating an activator in a manner responsive to the assay conditions may conveniently be housed in a housing, where the housing comprises means for controlling and/or adjusting the various elements of the device, such as on-off switches, toggle switches, dials and the like.

Figure 3A:
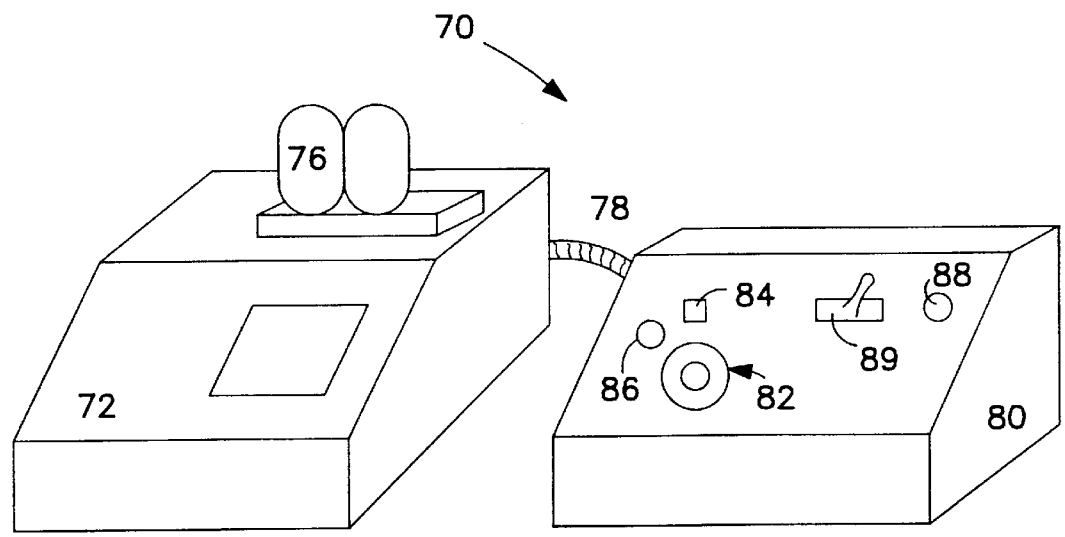
FIG. 3A shows an automatic device according to the subject invention.
Figure 3B:
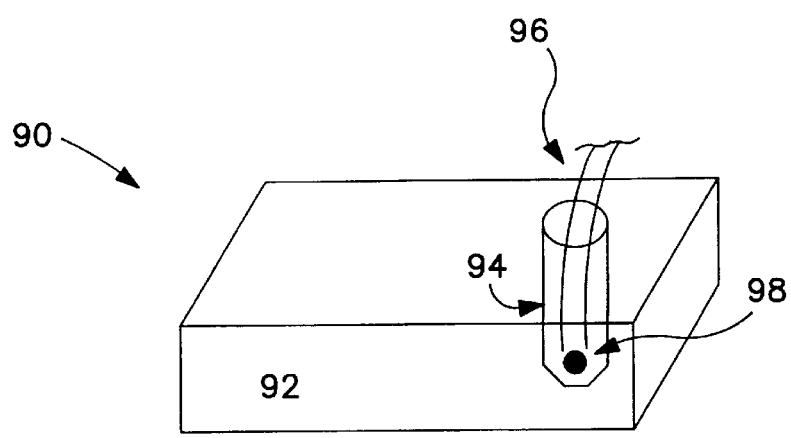
FIG. 3B shows an assay medium unit which is used in conjuction with the automatic device according to the subject invention.

An automatic device for performing the subject assay which incorporates a control circuit as described above is shown in FIG. 3. In FIG. 3, device 70 comprises thermocycler 72 and control box 80. Positioned over the sample holder (not shown) of the thermal cycler 72 is light bank 76 with which the assay medium in the sample holder shown in FIG. 3B is in light receiving relationship. Control box 80 is in electrical communication with thermocycler 72 via leads 78.

Control box 80 comprises dial 82 that adjusts the set temperature of the control circuit at which the light bank is activated by adjusting the potentiometer of the circuit. The toggle main switch 89 turns the control box on, as indicated by red LED 88, while push button switch 88 closes and activates the control circuit loop of the subject device, as indicated by illumination of green LED 86.

In FIG. 3B, assay medium unit 90, which is placed within the thermocycler 72 and is in light receiving relationship with light bank 76, comprises a tube holder 92 and an eppendorf tube or microtiter plate well 94 comprising the assay medium. Immersed in the assay medium is thermistor 98 which is in electrical communication with the control circuit of the device via leads 96.

Kits are provided having at least two pairs of probes, or ternary combinations of probes, where each pair may be in the same vessel. At least one pair will define a substantially contiguous sequence of a target nucleic acid and the other pair will be homologous, usually complementary, to the sequence of the first pair. Each probe has a side chain which forms a stem with the side chain of the other pair, so as to be capable of cross-linking as described previously. If desired, one or both of the probes may be labeled to allow for easy detection of cross-linked probes. One may use radioactive labels, fluorescent labels, specific binding pair member labels, and the like. The kits may have oligonucleotides which include sequences for hybridizing to a target nucleic acid or provide only the side chains for linking to such target homologous sequences. For the side chain sequences, these will have at least two nucleotides in addition to the cross-linking entity and usually not more than about 150, more usually not more than about 100, usually not more than about 60, depending upon whether a protective group is present. If the protective group is not present, the side chain by itself will usually not exceed 20 nucleotides, more usually not exceed about 12 nucleotides. The terminal nucleotide may be functionalized appropriately for linking to the target homologous sequence.

The following examples are offered by way of illustration and not by way of limitation.

EXPERIMENTAL

A. Preparation of the Photocrosslinker Reagent 1-O-(4,4'-Dimethoxytrityl)-3-O-(7-coumarinyl)-2-O-(β-cyanoethyl-N,N-diisopropyl phosphoramidite) glycerol The title compound, prepared in four steps starting from 7-hydroxycoumarin, is useful for incorporating the photocrosslinker into any position in the sequence of an oligonucleotide via automated synthesis.

Preparation of the Photocrosslinker Reagent 1-O-(4, 4'-Dimethoxytrityl)-3-O-(7-coumarinyl)-2-O-(b-cyanoethyl-N,N-diisopropyl phosphoramidite) glycerol The title compound, prepared in four steps starting from 7-hydroxycoumarin, is useful for incorporating the photocrosslinker into any position in the sequence of an oligonucleotide via automated synthesis.

Synthesis of 7-glycidyl Coumarin: To 270 mL acetone in a reaction flask equipped with a reflux condenser was added 7-hydroxycoumarin (16.2 g), epibromohydrin (15.8 g) and potassium carbonate (13.8 g) and the mixture was refluxed for 18 h. After cooling the reaction mixture, 100 mL 5% sodium hydroxide (aqueous) was added and the solution was extracted three times with 80 mL methylene chloride. The extracts were combined and the solvent removed by rotary evaporation to give the crude product as a yellow solid (1.5 g). The product was purified by recrystallization from hexane:acetone (3:2) at 4° C. to afford a white powder (290 mg): mp 110–112° C.; TLC (8% v/v ethyl acetate/chloroform) $R_f$=0.6.

Synthesis of 1-O-(7-coumarinyl) Glycerol: 7-Glycidyl coumarin (2.0 g) was dissolved in 80 mL acetone and 50 mL 1.8 M sulfuric acid, and the solution was refluxed for 20 minutes. The solution was cooled to room temperature, neutralized with 1.6 M ammonium hydroxide, and extracted three times with 50 mL ethyl acetate. The combined extracts were evaporated to yield the product as a white solid (1.40 g): mp 118–120° C.

Synthesis of 1-O-(4,4'-Dimethoxytrityl)-3-O-(7-coumarinyl) Glycerol: The starting material 1-O-(7-coumarinyl) glycerol (1.37 g) was dried by coevaporation with 11 mL pyridine, repeated three times. To the dried material was added 45 mL pyridine, 0.33 mL triethylamine, 4-dimethylaminopyridine (44 mg) and dimethoxytrityl chloride (1.78 g). The solution was stirred at room temperature for 3 h, 66 mL water was added, and the solution was extracted three times with 35 mL methylene chloride. The organic extract was dried with sodium sulfate and the solvent was removed to give the crude product. Purification by silica gel column chromatography using hexane:acetone:triethylamine (70:28:2) yielded the product as a white solid (2.6 g): TLC (same solvent) $R_f$=0.43.

Synthesis of 1-O-(4,4'-Dimethoxytrityl)-3-O-(7-coumarinyl)-2-O-(b-cyanoethyl-N,N-diisopropyl phosphoramidite) Glycerol: The starting material 1-O-(4,4'-Dimethoxytrityl)-3-O-(7-coumarinyl) glycerol was dried by coevaporation with 12 mL pyridine:chloroform (3:1), repeated twice. The resulting viscous liquid was dissolved in 10 mL pyridine: chloroform (1:1) and added under argon with rapid stirring to a flask containing 10 mL methylene chloride, 3 mL N,N-diisopropylethylamine, and b-cyanoethyl-N,N-diisopropyl chlorophosphoramidite (1.8 g). The solution was stirred for 90 minutes. The solution was diluted with 60 mL ethyl acetate and 3 mL triethylamine, then washed twice with 50 mL saturated aqueous sodium chloride. The organic phase was dried with sodium sulfate and the solvent was removed to give the crude product. Purification by silica gel column chromatography using hexane:acetone:triethylamine (70:28:2) yielded the product as a viscous, clear oil (2.6 g): TLC (hexane:acetone, 4:1) $R_f$=0.20.

Oligonucleotide Synthesis: For use in automated oligonucleotide synthesis, the photocrosslinking reagent was dissolved in dry acetonitrile at a concentration of 0.5 g/mL. The bottle of the solution was affixed to an extra port on the synthesizer and incorporated via the preprogrammed protocol. After automated synthesis, the oligonucleotide was cleaved from the solid support and deprotected with 3 mL 30% ammonium hydroxide for 2 h at room temperature. The ammonium hydroxide was removed in vacuo, and the oligonucleotide was purified to homogeneity by denaturing polyacrylamide gel electrororphoresis. Stock solutions in distilled, de-ionized water were prepared and stored until use at −20° C.

```
Sequences of nucleic acids employed in Examples
                        1 & 2

Nax 228 (SEQ ID NO:08)
        5'ATTTTGTCTTTGCGCACAGACGATCTATTT3'

Nax 229 (SEQ ID NO:09)
        3'TTTCGTTTGTCTGCTAGATAAA5'

Nax 230 (SEQ ID NO:10)
        3'TAAAACAGAAACGCGCGAXA5'

Nax 231 (SEQ ID NO:11)
        5'ATTTTGTCTTTGCGCGGCTTT3'

Nax 232 (SEQ ID NO:12)
        3'AXACGTTTGTCTGCTAGATAAA5'

Nax 233 (SEQ ID NO:13)
        3'TAAAACAGAAACGCGCGTTT5'
```

X = ethoxycoumarin

1. The Ability to Obtain Cross-linking with a Photoactivatable Probe was Investigated.

| Component, | | Sample, μl | | | | | | | | | | | | | | | |
|---|---|---|---|---|---|---|---|---|---|---|---|---|---|---|---|---|---|
| Nax | pm/μl* | 1 | 2 | 3 | 4 | 5 | 6 | 7 | 8 | 9 | 10 | 11 | 12 | 13 | 14 | 15 | 16 |
| $^{32}$P-228 | 0.5 | 2 | 2 | 2 | 2 | | | | | 2 | 2 | 2 | 2 | | | | |
| $^{32}$P-229 | " | | | | | 2 | 2 | 2 | 2 | | | | | | | | |
| $^{32}$P-233 | " | | | | | | | | | | | | | 4 | 4 | 4 | 4 |
| 228 | " | | | | | | 2 | | 2 | | | | | | | 2 | 2 |
| 229 | " | | 2 | | 2 | | | | | | | | | | | | |
| 230 | " | | | 2 | 2 | | | 2 | 2 | | | | | | | | |
| 232 | " | | | | | | | | | | 2 | | 2 | | 2 | | 2 |
| 233 | " | | | | | | | | | | | 2 | 2 | | | | |
| H$_2$O | | 12 | 10 | 10 | 8 | 12 | 10 | 10 | 8 | 12 | 10 | 10 | 8 | 10 | 8 | 8 | 6 |

*pmol/μl
Total volume = 32.5 μl

Protocol

Add 18.5 μl of 50:150 0.75M NaOH: 1×TE to 14 μl of sample.

Incubate at room temperature for 10 minutes.

Add 17.5 μl neutralization buffer: 3.5 μl of 3.5% BSA; 1.5 μl of 1.5M HOAc; 11.3 μl of 20×SSC and 0.4 μl of water.

Incubate at 40° C. for 15 minutes.

Irradiate at 30° C. for 1 hour (Stratalinker; thin pyrex filter)

PAGE 15% (with 7M urea)

The results of the PAGE showed that samples 3, 8 and 10 showed good cross-linking, but the band for sample 16 was light as compared to the other bands.

2. The Effect of Thermal Cycling on Cross-linking was Investigated.

| Component, | | Sample, μl | | | | | | | |
|---|---|---|---|---|---|---|---|---|---|
| Nax | pm/μl* | 1 | 2 | 3 | 4 | 5 | 6 | 7 | 8 |
| $^{32}$P-229 | 1 | 1 | 1 | 1 | 1 | | | | |
| $^{32}$P-233 | " | | | | | 1 | 1 | 1 | 1 |
| 228 | 0.02 | | 1 | | 1 | | 1 | | 1 |
| 230 | 0.5 | 2 | 2 | 2 | 2 | | | | |
| 232 | " | | | | | 2 | 2 | 2 | 2 |
| H$_2$O | | 11 | 10 | 11 | 10 | 11 | 10 | 11 | 10 |

*pmol/μl

Protocol

Add 18.5 μl of 50:150 0.75M NaOH: 1×TE to 14 μl of sample.

Incubate at room temperature for 10 minutes.

Add 17.5 μl neutralization buffer: 3.5 μl of 3.5% BSA; 1.5 μl of 1.5M HOAc; 11.3 μl of 20×SSC and 0.4 μl of water.

Incubate at 40° C. for 15 minutes.

Irradiate at 40° C. for 25 minutes (Stratalinker; thin pyrex filter)

Remove samples, 3,4,7,8, as before; heat to 88° C. for 1 minute.

Cycle:

Irradiate at 30° C. for 25 minutes.

Remove samples, heat to 88° C. for 1 minute.

Repeat cycle 3 times ending with irradiation

PAGE 17% (with 7M urea)

Based on the PAGE results, samples 1, 3, 5, and 7 showed that with or without thermocycling, in the absence of the target strand, the two probes do not significantly cross-link. Cross-linking was more efficient with probes 229 and 230. The extent of cross-linking was quantified for samples 2 and 4, where cross-linking was 2.3% and 7.8% respectively.

```
Sequences of Nucleic acids use in Examples 3-6:

Nax 238 (SEQ ID NO:14)
5'TTTATAAAAAGCTCGTAATATGCAAGAGCATTGTAAGCAGAAGACTTA3'

Nax 271 (SEQ ID NO:15)
5'TTTATAAAAAGCTCGTAATATGCTTTTTTTTT3'

Nax 270 (SEQ ID NO:16)
3'TTTTTTTTTCTCGTAACATTCGTCTTCTGAAT5'

Nax 272 (SEQ ID NO:18)
3'AAATATTTTCGAGCATTATACGAXA5'

Nax 273 (SEQ ID NO:19)
3'AAATATTTTCGAGCATTATACGAAAXA5'

Nax 274 (SEQ ID NO:20)
3'AAATATTTTCGAGCATTATACGAAXAAAA5'

Nax 275 (SEQ ID NO:21)
3'AAATATTTTCGAGCATTATACGAAAAAXA5'

Nax 239 (SEQ ID NO:22)
```

-continued

Sequences of Nucleic acids use in Examples 3–6:

3'AAATATTTTTCGAGCATTATACGTTCTCGTAACATTCGTCTTCTGAAT5'

Nax 278 (SEQ ID NO:23)
3'TAAATATTTTTCGAGCATTATACGTTCAAGTAACATTCGTCTTCTGAAT5'

Nax 277 (SEQ ID NO:24)
3'AAATATTTTTCGAGCATTATACGTTCTTTTTTTTT5'

Nax 276 (SEQ ID NO:25)
5'TTTTTTTTTCATTGTAAGCAGAAGACTTA3'

Nax 279 (SEQ ID NO:26)
5'TTTATAAAAAGCTCGTAATATGCAAGAAXAAAA3'

Nax 280 (SEQ ID NO:27)
5'TTTATAAAAAGCTCGTAATATGCAAGAXAAAAA3'

The Effect of Having the Reactive Group at the 5' Terminus was Investigated.

| Component, Nax | ppm/μl* | Sample, μl | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| $^{32}$P-270 | 0.5 | | 2 | 2 | | | | | 2 | 2 | | 2 | 2 |
| 238 | " | | | 1 | | | 1 | | | 1 | | | | 1 |
| 271 | " | 2 | | | 2 | | | 2 | | | 2 | | |
| 272 | " | 1 | 1 | 1 | | | | | | | | | |
| 273 | " | | | | 1 | 1 | 1 | | | | | | |
| 274 | " | | | | | | | 1 | 1 | 1 | | | |
| 275 | " | | | | | | | | | | 1 | 1 | 1 |
| H$_2$O | | 11 | 11 | 9 | 11 | 11 | 9 | 11 | 11 | 9 | 11 | 11 | 9 |

*pmol/μl

Protocol

Add 18.5 μl of 50:150 0.75M NaOH: 1×TE to 14 μl of sample into 96 well CoStar.

Incubate at room temperature for 10 minutes.

Add 17.5 μl neutralization buffer: 3.5 μl of 3.5% BSA; 1.5 μl of 1.5M HOAc; 11.34 μl of 20×SSC and 0.4 μl of water.

Add 75 μl mineral oil to inhibit evaporation.

Incubate at 40° C. for 20 minutes.

Irradiate at 40° C. for 20 minutes (UV-A lamp, UV-32 Hoya filter) PAGE 20% with 7M urea.

The percent cross-linking with the reactive entity at the 5' terminus was: 1, 80%; 3, 69%; 4, 57%; 6, 69%; 7, 68%; 9, 80%; 10, 38%; and 12, 67%. There was no significant cross-linking observed where there was no template.

4. The Effect of Having the Reactive Group at the 3' Terminus was Investigated.

| Component, Nax | pm/μl* | Sample, μl | | | | | | | |
|---|---|---|---|---|---|---|---|---|---|
| | | 1 | 2 | 3 | 4 | 5 | 6 | 7 | 8 |
| $^{32}$P-276 | 0.5 | | 2 | 2 | 2 | | 2 | 2 | 2 |
| $^{32}$P-277 | " | 2 | | | | 2 | | | |
| 239 | " | | | 1 | | | | 1 | |
| 278 | " | | | | 1 | | | | 1 |
| 279 | " | 1 | 1 | 1 | 1 | | | | |
| 280 | " | | | | | 1 | 1 | 1 | 1 |
| H$_2$O | | 11 | 11 | 10 | 10 | 11 | 11 | 10 | 10 |

*pmol/μl

Protocol

The protocol was the same as the previous example, except that the PAGE was 18%.

The percent cross-linking with the reactive entity at the 3' terminus was: 1, 86%; 3, 73%; 4, 83%; 5, 79%; 7, 42%; and 8, 77%. There was no significant cross-linking observed where there was no template.

5. The Time Dependency of Cross-linking Efficiency was Determined.

| Component, Nax | pm/μl* | 1 | 2 | 3 | 4 | 5 | 6 | 7 | 8 |
|---|---|---|---|---|---|---|---|---|---|
| $^{32}$P-270 | 0.5 | 2 | | 2 | | 2 | | 2 | |
| $^{32}$P-276 | " | | 2 | | 2 | | 2 | | 2 |
| 238 | 5 | 1 | | 1 | | 1 | | 1 | |
| 274 | " | 1 | | 1 | | 1 | | 1 | |
| 278 | " | | 1 | | 1 | | 1 | | 1 |
| 279 | " | | 1 | | 1 | | 1 | | 1 |
| H$_2$O | | 10 | 10 | 10 | 10 | 10 | 10 | 10 | 10 |

*pmol/μl

Protocol

The above protocol was followed to the incubation at 40° C. for 15 minutes, where irradiation was then carried out for 20 minutes, with samples 1 and 2 being removed after 5 minutes, 3 and 4 after the next 5 minutes, and so on, followed by PAGE 20% with 7M urea.

The percent cross-linking observed was: sample 1, 65%; 2, 72%; 3, 76%; 4, 80%; 5, 80%; 6, 83%; 7, 82%; and 8, 84%. The odd-numbered samples had the reactive group on the 5' terminus, while the even numbered samples had the reactive group on the 3' terminus. The results indicate that after 10 minutes there does not seem to be any change in the degree of cross-linking and that there is no significant difference in result, whether the reactive group is on the 5' or 3' terminus.

6. The Effect of Variation in Concentration of the Probes was Investigated.

| Component, Nax | pm/μl* | Sample, μl | | | | | | | |
|---|---|---|---|---|---|---|---|---|---|
| | | 1 | 2 | 3 | 4 | 5 | 6 | 7 | 8 |
| $^{32}$P-276 | 0.5 | 2 | 2 | 2 | 1 | 1 | 1 | 1 | 1 |
| 278** | | 1 | 2 | 2 | 2 | 1 | 5 | 2.5 | 1 |
| 279 | 0.5 | 2 | 2 | 2 | 2 | 2 | 2 | 2 | 2 |
| H$_2$O | | 10 | 8 | 8 | 9 | 10 | 6 | 8.5 | 10 |

*pmol/μl
**278 was 5 pmol/μl for sample 1,
0.5 pmol/μl for samples 2–5, and
0.02 pmol/μl for samples 6 to 8.

Protocol

The sample was prepared as previously described, followed by incubation at 40° C. for 10 minutes. Samples 1 and 2 were removed from the plate and put in Robbins Scientific PCR tubes (clear) and capped. The PCR tubes were laid across the top of a 96-well plate and irradiated 20 minutes (UV-A, UV-32). The samples were analyzed with PAGE 20% with 7M urea.

The degree of cross-linking observed in the samples was as follows: sample 1, 83%; 2, 81%; 3, 79%, 4, 82%; 5, 78%; 6, 17%; 7, 8.2%; and 3.9%. At 0.1 pmol of the probe, the degree of cross-linking has significantly diminished, but even at 0.05 pmol, cross-linking is still discernible. The effect results from a combination of a lower concentration of the probe and lower mole ratio of the probe to template.

7. Use of Cross-linked Probes as a Template was Investigated.

Cross-linked products were prepared on a preparative scale and isolated and purified using PAGE. The five cross-linked products were 345-346, 386-346, 387-346, 388-346, and 389-346.

8. Linear Amplification is Demonstrated in the Following Two Exemplifications.

Example A

| Component, | | Sample, μl | | | | | | | |
|---|---|---|---|---|---|---|---|---|---|
| Nax | pm/λ* | 1 | 2 | 3 | 4 | 5 | 6 | 7 | 8 |
| $^{32}$P-276 | 0.5 | 1 | 1 | 1 | 1 | 1 | 1 | 1 | 1 |
| 278 | .005 | 1 | 1 | 1 | 1 | 1 | 1 | 1 | # |
| 279 | 0.5 | 2 | 2 | 2 | 2 | 2 | 2 | 2 | 2 |
| H$_2$O | | 10 | 10 | 10 | 10 | 10 | 10 | 10 | 10 |
| Conditions | | | | | | | | | |
| No. irradiations | | 1 | 5 | 5 | 10 | 10 | 15 | 15 | 15 |

Nucleic Acid Sequences used in Example 7.

NAX 342 (SEQ ID NO:27)
5'-GATATCGGATTTACCAAATACGGCGGGCCCGCCGTTAGCTAACGCTAATCGATT

NAX 345 (SEQ ID NO:28)
5'-AAAAAXAGCCGTTAGCTAACGCTAATCGATT

NAX 346 (SEQ ID NO:29)
5'-GATATCGGATTTACCAAATACGGCGGGCCCTTTTTTT

NAX 347 (SEQ ID NO:30)
5'-AAAAAXAGCCGTATTTGGTAAATCCGATATC

NAX 348 (SEQ ID NO:31)
5'-AATCGATTAGCGTTAGCTAACGGCGGGCCCTTTTTTT

NAX 386 (SEQ ID NO:32)
5'-AAAXAAGCCGTTAGCTAACGCTAATCGATT

NAX 387 (SEQ ID NO:33)
5'-AAXAAAGCCGTTAGCTAACGCTAATCGATT

NAX 388 (SEQ ID NO:34)
5'-AXAAAAGCCGTTAGCTAACGCTAATCGATT

NAX 389 (SEQ ID NO:35)
5'-XAAAAAGCCGTTAGCTAACGCTAATCGATT

| Component, | pmol/mL | Sample [mL] | | | | | |
|---|---|---|---|---|---|---|---|
| NAX | | 1 | 2 | 3 | 4 | 5 | 6 |
| $^{32}$P-348 | 0.5 | 1 | 1 | 1 | 1 | 1 | 1 |
| 342 | 5 | 1 | | | | | |
| 345–346 | 2.5 | | 2 | | | | |
| 386–346 | " | | | 2 | | | |
| 387–346 | " | | | | 2 | | |
| 388–346 | " | | | | | 2 | |
| 389–346 | " | | | | | | 2 |
| 347 | 5 | 1 | 1 | 1 | 1 | 1 | 1 |
| H$_2$O | | 11 | 10 | 10 | 10 | 10 | 10 |

Protocol

The samples were prepared as previously described, except only 70 mL of mineral oil was employed. The samples were incubated at 40° C. for 20 minutes. The samples were then irradiated at 40° C. for 20 minutes, followed by analysis by PAGE, 17% polyacrylamide and 7 M urea.

The percent cross-linking as a result of the cross-linked probes acting as a template in comparison with a single-stranded template is as follows: sample 1, 73%; 2, 75%; 3, 71%; 4, 69%; 5, 66%; and 6, 67%. The results demonstrate that the cross-linked probes can serve as a template for cross-linking a hybridized probe pair as effectively as a single-stranded target can serve as a template.

-continued

| Component, | | Sample, μl | | | | | | | |
|---|---|---|---|---|---|---|---|---|---|
| Nax | pm/λ* | 1 | 2 | 3 | 4 | 5 | 6 | 7 | 8 |
| Heat treatment | | — | Δ | + | Δ | + | Δ | + | + |

*pmol/λ;
add 0.2λ of 0.5 pmol/λ after 10 irradiations
Δ heat cycle set forth below;
+ isothermal Protocol The samples were prepared as previously described, with the probes at 100-fold excess over the target sequence.

The reagents were combined in 0.2 ml PCR tubes from MJ Research and covered with 60 µl mineral oil.

All incubations were done on a PTC-100 thermal controller from MJ Research.

The assay mixture was incubated at 40° C. for 15 minutes.

Irradiation was for 15 minutes (Autoprobe, 40° C., UV-A, UV-32).

Samples 2, 4, and 6 were treated in PTC-100 (Program name PCA 8640, 4 minutes at 86° C.; 11 minutes at 40° C.)

Samples 3, 5, 7, 8 were left at room temperature.

The irradiation was repeated, with samples 2, 3 being removed after 5 irradiations, cycling continued, but with the following schedule: irradiation time: 5 minutes; heating time: 2 minutes at 86° C.; incubation time: 5 minutes at 40° C.

Some cloudiness was observed in samples 4 and 6 after the 6th cycle. The heating temperature was reduced to 82° C. for the 7th heating cycle.

PAGE 17% 7M urea.

The following table indicates the results.

C. for 7 minutes. Samples 6, 7 and 8 received 10 cycles of irradiation with 9 intervening cycles of remaining in the mineral bath inside the Stratalinker. The following table indicates the results.

| Sample | % Cross-linked | Total # Counts | Unreacted | Cross-linked | Cycles |
|---|---|---|---|---|---|
| 1 | 1.6 | 11641 | 11458 | 183 | 1 |
| 2 | 2.2 | 16744 | 16381 | 363 | 10 |
| 3 | 11.7 | 11190 | 9883 | 1307 | " |
| 4 | 9.5 | 15468 | 13993 | 1475 | " |
| 5 | 8.0 | 17118 | 15759 | 1359 | " |
| 6 | 2.0 | 15260 | 14954 | 306 | "* |
| 7 | 2.2 | 14000 | 13687 | 313 | "* |
| 8 | 1.8 | 17925 | 17595 | 330 | "* |

*No denaturation

Sample 3 showed approximately 12% cross-linking, while sample 6 showed about 2% cross-linking, indicating an approximately 6-fold linear amplification.

9. Linear Amplification Using Non-isotopic Detection, Multiple Probe Sets, and Automated Cycling Example B

| Sample | % cross-linked | Total # Counts | Unreacted | Cross-linked | Cycles |
|---|---|---|---|---|---|
| 1 | 1.2 | 11754 | 11607 | 147 | 1 |
| 2 | 6.6 | 7027 | 6563 | 464 | 5 |
| 3 | 2.8 | 8272 | 8037 | 235 | " |
| 4 | 8.0 | 7094 | 6528 | 566 | 10 |
| 5 | 2.9 | 7953 | 7722 | 231 | " |
| 6 | 9.4 | 7280 | 6595 | 685 | 15 |
| 7 | 4.0 | 7020 | 6734 | 286 | " |
| 8 | 23 | 7000 | 5418 | 1582 | " |

| Component, Nax | pm/ λ* | Sample, µl | | | | | | | |
|---|---|---|---|---|---|---|---|---|---|
| | | 1 | 2 | 3 | 4 | 5 | 6 | 7 | 8 |
| $^{32}$P-276 | 0.5 | 2 | 2 | 2 | 2 | 2 | 2 | 2 | |
| 278 | .02 | .8 | .8 | .8 | .8 | .8 | .8 | .8 | .8 |
| 279 | 0.5 | 2.5 | 2.5 | 2.5 | 2.5 | 2.5 | 2.5 | 2.5 | 2.5 |
| H$_2$O | | 9 | 9 | 9 | 9 | 9 | 9 | 9 | 9 |
| Conditions | | | | | | | | | |
| No. irradiations | | 1 | 2 | 10 | 10 | 10 | 10 | 10 | 10 |
| Heat treatment | — | Δ | Δ | Δ | Δ | + | + | + | |

*pmol/λ;
Δ heat cycle set forth below;
+ isothermal

Protocol

The above procedure was repeated with some modifications. The probe was in 50-fold excess to the target. 75 µl of mineral oil was used. The reactions were run in a polycarbonate plate. Incubation and heating were on a MJ Research PTC-100 instrument. Irradiation was in a Stratalinker with the heating provided by a mineral oil bath set at 40° C.

Sample 1 was removed after one cycle of irradiation and heating; sample 2 was removed after one cycle of irradiation, heating and an additional irradiation. Samples 3, 4 and 5 received 10 cycles of irradiation of 10 minutes each, with 9 intervening thermal denaturation cycles in accordance with the following schedule: 84° C. for 3 minutes; 40°

Nucleic Acid Sequences

NAX 595 (SEQ ID NO:41)
5'-TTTTTTCCAAGGAGGTAAACGCTCCTCTGB

NAX 596 (SEQ ID NO:42)
5'-FATTGGTTGATCGCCCAGACAATGCAXA

NAX 601 (SEQ ID NO:43)
5'-TTTTTTTCCCTTTATACGCTCAAGCAATAB

NAX 602 (SEQ ID NO:44)
5'-FTCTTTGCTATAGCACTATCAAGCCAXA

NAX 607 (SEQ ID NO:45)
5'-TTTTTTGTCTCGAACATCTGAAAGCATGGB

NAX 608 (SEQ ID NO:46)
5'-FCTGCGTCTTGCTCTATTTGACCGCAXA

NAX 613 (SEQ ID NO:47)
5'-TTTTTTTTGAGCGGCTCTGTCATTTGCCCAB

NAX 614 (SEQ ID NO:48)
5'-FTGTCCAAGGATTATTTGCTGGTCCAXA

| Component, NAX | pmol/mL | Sample [mL] | | | |
|---|---|---|---|---|---|
| | | 1 | 2 | 3 | 4 |
| 595 | 1 | | | 0.375 | 0.375 |
| 596 | " | | | 0.125 | 0.125 |
| 601 | " | 0.375 | 0.375 | 0.375 | 0.375 |
| 602 | " | 0.25 | 0.25 | 0.125 | 0.125 |
| 607 | " | | | 0.375 | 0.375 |
| 608 | " | | | 0.125 | 0.125 |
| 613 | " | 0.375 | 0.375 | 0.375 | 0.375 |
| 614 | " | 0.25 | 0.25 | 0.125 | 0.125 |
| H$_2$O | | 12.75 | 12.75 | 12 | 12 |
| lysis buffer* | | 18.5 | 16.5 | 18.5 | 16.5 |
| target DNA** | $10^{-5}$ | | 2 | | 2 |

X = ethoxycoumarin
F = fluorescein
B = biotin
*Lysis buffer = 1:3 0.75M NaOH:1X TE (pH 7.5).
**The target DNA is the Chlamydia cryptic plasmid cloned into pBluescript, pretreated by boiling for 30 minutes in lysis buffer.

Add 17.5 mL of neutralization buffer (1.75 mL of 3.5% BSA, 1.5 mL of 1.5 M HOAc, 11.3 mL of 20×SSC, and 2.15 mL of water) to each sample, loaded in a 96-well polycarbonate plate. Add 50 mL mineral oil to prevent evaporation.

The plate was put onto a programmable thermal controller beneath a bank of UV-A lamps. The thermal controller was programmed to bring the samples through the following temperature profile: (1) 60° C. for 10 minutes; (2) 85° C. for 90 seconds; (3) 58° C. for 5 minutes; (4) 55° for 5 minutes; (repeat steps 2,3,4 five times); (5) hold at 20° C. The operation of the bank of lamps was controlled via a control circuit that responds to the temperature sensed by a thermistor. The thermistor was embedded in one of the wells in the 96-well plate. The control circuit activated the light bank if the temperature sensed by the thermistor was within a narrow range (approximately ±3° C.) about a desired temperature, in this case 55° C.

Following the cycling procedure the mineral oil was separated from the aqueous sample, and hereafter the aqueous sample was treated to: incubation with streptavidin-coated magnetic particles, five repetitions of removal of the supernatant liquid and addition of buffered wash solution, incubation with an anti-fluorescein/alkaline phosphatase conjugate, five repetitions of removal of the supernatant liquid and addition of buffered wash solution, and incubation with Attophos at 37° C. The fluorescent signal generated in each sample was measured (relative fluorescence units): Sample 1, 39; 2, 142; 3, 58; 4, 250. The results demonstrate that a multitude of probe sets can be combined to achieve a higher signal and that the amplification process can be carried out by automated methods.

10. Nucleic Acid Sequence Detection of Chlamydia Trachomatis in Clinical Samples Using an Amplification Probe Set

| Component, | | Sample [mL] | | | |
|---|---|---|---|---|---|
| NAX | pmol/mL | 1 | 2 | 3 | 4 |
| 601 | 1 | 1.2 | 1.2 | 1.2 | 1.2 |
| 602 | " | 0.8 | 0.8 | 0.8 | 0.8 |
| lysis buffer | | | | 37 | 37 |
| clinical sample* | | 37 | 37 | | |
| $H_2O$ | | 26 | 26 | 26 | 26 |

*clinical samples were obtained by endocervical swab. The swabs were boiled in a tube with 400 mL of lysis buffer for 30 minutes. For each sample, 37 mL of lysate was removed for testing.

Samples 1 and 2 are from two different patients, and samples 3 and 4 are negative controls for the experiment.

Add 35 mL of neutralization buffer (1.75 mL of 3.5% BSA, 1.5 mL of 1.5 M HOAc, 11.3 mL of 20×SSC, and 2.15 mL of water) to each sample, loaded in a 96-well polycarbonate plate. Add 50 mL mineral oil to prevent evaporation.

The previous protocol was followed for amplification and detection, except that the time at 58° C. was 9 minutes and the time at 55° C. was 6 minutes in each thermal cycle. The fluorescent signal generated in each sample was measured (relative fluorescence units): Sample 1, 768; 2, 43; 3, 44; 4, 53. Sample 1 was assigned as positive for the presence of C. trachomatis and sample 2 was assigned as negative. These results were confirmed by PCR and culture. The results demonstrate the effectiveness of the amplification procedure for the detection of nucleic acid sequences in clinical specimens.

11. Geometric Amplification is Demonstrated in the Following Exemplifications.

```
Nucleic Acid Sequences

NAX 441 (SEQ ID NO:36)
5'-GATTTAAAAACCAAGGTCGATGTGATAGGGCTCGTATGTGGAATGTCGAACTCATCGGCGAT

NAX 443 (SEQ ID NO:37)
5'-GGGCGAGAXATATCACATCGACCTTGGTTTTTAAATC

NAX 444 (SEQ ID NO:38)
5'-GATTTAAAAACCAAGGTCGATGTGATAGGGCTCGAXAAAAA

NAX 445 (SEQ ID NO:39)
5'-TCGCCGATGAGTTCGACATTCCACATACGAGCCCTTTCTCG

NAX 446 (SEQ ID NO:40)
5'-TTTTTTTTATGTGGAATGTCGAACTCATCGGCGA
```

| Component, Nax | pm/µl | Samples, µl | | | | | | | |
|---|---|---|---|---|---|---|---|---|---|
| | | 1 | 2 | 3 | 4 | 5 | 6 | 7 | 8 |
| $^{32}P$-443 | 1 | 1 | 1 | 1 | 1 | 1 | 1 | 1 | 1 |
| 444 | 1 | | | | | 1 | 1 | 1 | 1 |
| 445 | .36 | 2.8 | 2.8 | 2.8 | 2.8 | 2.8 | 2.8 | 2.8 | 2.8 |
| 446 | 1 | | | | | 1 | 1 | 1 | 1 |
| 441 | 10 fmol/µl | 1 | 1 | 1 | 1 | 1 | 1 | 1 | 1 |
| $H_2O$ | | 9.2 | 9.2 | 9.2 | 9.2 | 9.2 | 9.2 | 9.2 | 9.2 |
| Conditions | | | | | | | | | |
| No. irradiations | | 1 | 3 | 5 | 7 | 1 | 3 | 5 | 7 |
| Heat treatment | | Δ | Δ | Δ | Δ | Δ | Δ | Δ | Δ |

Δ heat cycle set forth below

The following control samples were also run:

| Component, | | Samples, µl | | | |
|---|---|---|---|---|---|
| Nax | pm/µl | 9 | 10 | 11 | 12 |
| $^{32}$P-443 | 1 | 1 | 1 | 1 | 1 |
| 444 | 1 | | 1 | | 1 |
| 445 | .36 | 2.8 | 2.8 | 2.8 | 2.8 |
| 446 | 1 | 1 | | | 1 |
| 441 | 10 fmol/µl | 1 | 1 | | |
| H$_2$O | | 9.2 | 7.2 | 10.2 | 8.2 |
| Conditions | | | | | |
| No. irradiations | | 7 | 7 | 7 | 7 |
| Heat treatment | | + | + | Δ | Δ |

Δ heat cycle set forth below
+ = isothermal

Protocol

Add 18.5 µl of 1:3 075 M NaOH:1×TE to sample in a microtitre plate.

Add 17.5 µl neutralization buffer (3.5 µl of 3.5% BSA; 1.5 µl of 1.5M HOAc; 11.3 µl of 20×SSC and 0.4 µl of water) to each well.

Layer 50 µl mineral oil on top of each well to inhibit evaporation.

Incubate 20 minutes at 40° C.
Irradiate at 40° C. for 20 minutes. (UV-A light source)
Denature for 2 minutes at 90° C.
Analysis by 10% PAGE with 7M urea.
Bands were excised and the amount of $^{32}$p in each band was quantified by scintillation counting.

Results

The results are summarized in the following table.

| Sample | Total Counts | Counts in Starting Material | Counts in Product | % Conversion to Product |
|---|---|---|---|---|
| 1 | 5218 | 5201 | 17 | 0.3 |
| 2 | 5437 | 5382 | 55 | 1.0 |
| 3 | 5083 | 5019 | 64 | 1.3 |
| 4 | 5156 | 5081 | 75 | 1.6 |
| 5 | 4846 | 4827 | 19 | 0.4 |
| 6 | 4777 | 4708 | 69 | 1.4 |
| 7 | 4859 | 4706 | 153 | 3.1 |
| 8 | 4830 | 4471 | 359 | 7.4 |
| 9 | 5629 | 5616 | 13 | 0.2 |
| 10 | 5486 | 5429 | 57 | 1.0 |
| 11 | 5548 | 5543 | 5 | <1 |
| 12 | 5536 | 5517 | 19 | 0.3 |

The results demonstrate that by employing two complementary sets of probes, a geometric amplification of the signal indicative of the presence of the target nucleic acid may be obtained.

12. The Use of a Fith Probe as a Protective System is Demonstrated

Nucleic Acid Sequences:

NAX 442 (SEQ ID NO:49)
5'-ATCGCCGATGAGTTCGACATTCCACATACGAGCCCTATCACATCGACCTTGGTTTTTAAATC

NAX 562 (SEQ ID NO:50)
5'-AAAGGGCTCGAAAAA

| Component, | | Sample [µl] | | | |
|---|---|---|---|---|---|
| NAX | pmol/µl | 1 | 2 | 3 | 4 |
| $^{32}$P-446 | 0.52† | 1.9 | 1.9 | 1.9 | 1.9 |
| 443 | 1 | 1 | 1 | 1 | 1 |
| 444 | 1 | 1 | 1 | 1 | 1 |
| 445 | 1 | 1 | 1 | 1 | 1 |
| 562 | 1 | | 1 | | |
| 562 | 10 | | | 1 | 1 |
| 442 | 10$^{-4}$ | | | | 1 |
| H$_2$O | | 9.1 | 8.1 | 8.1 | 7.1 |

†prepared from 1.0 µl of 0.1 pmol/µl $^{32}$P-446 and 0.9 µl of 1.0 pmol/µl 446

Protocol:

Add 18.5 µl of 1:3 0.75M NaOH: 1×TE (pH7.5) to each sample, loaded in a 96-well microtitre plate.

Add 17.5 µl of neurtalization buffer (1.75 µl of 3.5% BSA, 1.54 µl of 1.5 M HOAc, 11.3 µl of 20×SSC, and 2.15 µl of water) to each sample. Add 50 µl mineral oil to prevent evaporation.

Incubate at 55° C. for 15 minutes.

Perform 30 cycles of: incubated at 46° C. for 1 minute; irradiate with UV-A light at 43° C. for 7 minutes: and denature at 90° C. for 1 minute.

The samples analyzed by denaturing PAGE (13% with 7M urea).

The degree of product formed (NAX 446 crosslinked to NAX 444) as observed by gel electrophoresis and quantification by scintillation counting was: 1, 8.0%; 2, 2.7%; 3,1.3%; 4,23%. The results demonstrate that the fifth probe (NAX 562 suppresses the occurrence of a target independent reaction, and does not prevent the target specific amplification from occurring.

13. Chemical Amplification Using a Coordination Complex as the Crosslinker

Another class of crosslinking agents that are useful for covalently crosslinking two probes comprises metal coordination complexes. Activation of the metal complex may be either photonic or thermal. The activated complex may then react by substitution, addition, or cyclization with an appropriate reactant situated on the opposite strand in the stem, and the two probes are covalently crosslinked as a result of the new coordination complex produced.

For example, platinum(II) complexes are useful for forming complexes with amine ligands as well as nucleic acid bases, especially guanine and adenine. These complexes undergo thermal substitution reactions, and square planar Pt(II) complexes are known to photodissociate upon UV irradiation and subsequently add a ligand.

Photocrosslinking

A crosslinker probe is prepared with a platinum complex adduct at a specific site in the stem region, and a recipient probe is prepared with an appropriate ligand to react with the photoactivated complex, for example, an alkylamine, spatially situated for optimal contact with the platinum complex.

Example. Probes with the following sequences are prepared:

```
NAXP 019 (SEQ ID NO:51)
5'-TCTTTATTTAGATATAGAATTTCTTTTTTAGAGAGTTTAGAAGAAT

NAXP 020 (SEQ ID. 52)
5'-ATTCTTCTAAACTCTCTAAAAAACAAG'G'AA

NAXP 021 (SEQ ID. 53 )
5'TT*CCT*TGGAAATTCTATATCTAAATAAAGA

NAXP 022 (SEQ ID. 54)
5'-ATTCTTCTAAACTCTCTAAAAAACAAG'AA

NAXP 023 (SEQ ID. 55)
5'-TT*CT*TGGAAATTCTATATCTAAATAAAGA

T* = amine ligand-containing base: 2'-deoxy-5-(b-
aminoethoxymethyl)uridine
G' = site of Pt adduct
Underlined bases comprise the stem-forming portion of
the oligonucleotide
```

NAXP 019 is homologous to the—strand of the Chlamydia cryptic plasmid, complementary to the+strand, postion 3878–3900.

Preparation of recipient probes (NAXP 021, NAXP 023). The amine ligand-containing base is prepared according to Baker et.al., *J. Med. Chem.* (1966), 9, 66, from 2'-deoxyuridine and N-trifluoroacetyl-2-aminoethanol. The fully protected N-trifluoroacetyl-5'-O-dimethoxytrityl-3'-O-phosphoramidite is prepared by standard techniques. The oligonucleotide is then prepared by standard automated synthesis techniques. Deprotection of the aminoethyl ether occurs during deprotection of the oligonucleotide by treatment with 40% aqueous ammonia. The oligonucleotide is isolated by denaturing polyacrylamide gel electrophoresis. The band containing the product is excised, extracted into water, and purified and desalted by passage through a Sephadex G25 column. The oligonucleotide is reconstituted in a known volume of distilled water and the concentration determined by the absorbance at 260 nm.

Preparation of crosslinker probes (NAXP 020, NAXP 022). In NAXP 020, G'G' represents the bidentate adduct cis-[Pt(NH$_3$)$_2${d(GpG)-N7(G$_{27}$),-N7(G$_{28}$)}], and in NAXP 022, G' represents the monodentate adduct [Pt(NH$_3$)$_3${d(G)-N7(G$_{27}$)}]. NAXP020 is prepared by the reaction of the oligonucleotide (purified as stated above) with the diaqua compound cis-[Pt(NH$_3$)$_2$(H$_2$O)$_2$]$^{2+}$ at 37° C. for 18 hours, an NAXP 022 is prepared by the reaction of the oligonucleotide (purified as stated above) with the monoaqua compound [Pt(NH$_3$)$_3$(H$_2$O)]$^{2+}$ at 37° C. for 18 hours. Each of the products is obtained by anion exchange HPLC and desalted by dialysis.

The Ability to form Crosslinks with a Pt Adduct Between Probes in a Templated Reaction

| Component, NAXP | pmol/mL | Sample [mL] | | | | | | | | |
|---|---|---|---|---|---|---|---|---|---|---|
| | | 1 | 2 | 3 | 4 | 5 | 6 | 7 | 8 | 9 |
| $^{32}$P-019 | 0.2 | | | | | 1 | 1 | 1 | | |
| $^{32}$P-020 | 0.2 | 1 | 1 | | | | | | 1 | |
| $^{32}$P-021 | 0.2 | | | 1 | 1 | | | | | 1 |
| 019 | 1 | | | 1 | | 1 | | | 1 | 1 |
| 020 | 1 | | | | 1 | | 1 | | 1 | 1 |
| 021 | 1 | | 1 | | | | | 1 | 1 | 1 |
| H$_2$O | | 12 | 12 | 12 | 12 | 12 | 12 | 11 | 11 | 11 |

Protocol:

Add 18.5 mL of 1:3 0.75M NaOH: 1×TE (pH 7.5) to each sample, loaded in a 96-well microtitre plate.

Add 17.5 mL of neutralization buffer (1.75 mL of 3.5% BSA, 1.5 mL of 1.5 M HOAc, 11.3 mL of 20×SSC, and 2.15 mL of water) to each sample. Add 60 mL mineral oil to prevent evaporation.

Incubate at 40° C. for 15 minutes.

Irradiate at 40° C. for 20 minutes using UV-A lamps (sharp cut-off filter at 300 nm)

Analyze by denaturing PAGE (15% with 7 M urea)

The Effect of Thermal Cycling on the Amount of Crosslinked Product Formed

| Component, NAXP | pmol/mL | Sample [mL] | | | | | | | |
|---|---|---|---|---|---|---|---|---|---|
| | | 1 | 2 | 3 | 4 | 5 | 6 | 7 | 8 |
| $^{32}$P-021 | 0.2 | 1 | 1 | 1 | 1 | 1 | 1 | 1 | 1 |
| 019 | 0.01 | | | 1 | 1 | | | 1 | 1 |
| 020 | 1 | 1 | 1 | 1 | 1 | 1 | 1 | 1 | 1 |
| 021 | 1 | 1 | 1 | 1 | 1 | 1 | 1 | 1 | 1 |
| H$_2$O | | 11 | 11 | 10 | 10 | 11 | 11 | 10 | 10 |
| No. cycles | | 1 | 2 | 1 | 2 | 5 | 5 | 5 | 5 |
| thermal treat. | | + | D | + | D | + | D | + | D |

+ = isothermal, no denaturation
D = samples denatured each cycle

Protocol:

The sample preparation is the same as above. After an initial incubation for 10 minutes at 40° C. the samples were treated as indicated in the table.

Cycle:

Irradiate at 40° C. for 10 minutes

Heat to 85° C. for 2 minutes

Incubate at 40° C. for 10 minutes

Repeat the cycle procedure the indicated number of times, ending with the irradiation step at that cycle number.

Analyze by denaturing PAGE (15%, with 7 M urea)

The analogous set of experiments are performed using the monodentate adduct as the crosslinking probe, NAXP 022, the recipient probe NAXP 023, and the synthetic target NAXP 019.

Thermal Crosslinking Reaction

A crosslinker probe is prepared with a platinum complex adduct at a specific site in the stem region, and a recipient probe is prepared with an appropriate ligand to react with the complex, for example, a sulfur-containing ligand, spatially situated for optimal contact with the platinum complex.

Example. Probes with the following sequences are prepared:

NAXP 024 (SEQ ID. 56)
5'-ATTCTTCTAAACTCTCTAAAAAACAAMAA

NAXP 025 (SEQ ID. 57)
5'-TTLTTGGAAATTCTATATCTAAATAAAGA

M=a Pt or Pd square planar complex, (L$_3$)MX, where L$_3$ is a tridentate ligand with linking arm joined to the oligo backbone and X is a ligand chosen from $OH_2$, $Cl^-$, $Br^-$, $I^-$, $N^-$, $SCN^-$, $NO_2^-$, $NH_3$, pyridine, and the like. $L_3$ may be a terpyridinyl or diethylenetriamine derivative.

L=4-thiouridine, 2'-deoxy-4-thiouridine, 4-thiothymidine, (the 2,4-dithio analogues of these), non-nucleosidic group containing a mercapto group.

Include excess X in the solution to suppress substition reactions at the metal complex when it is not hybridized in the stem. The rate of the substitution reaction can be varied by the choice of the metal, (Pd faster than Pt), or the choice of the fourth ligand X (reactivity follows in the order listed above, fastest to slowest).

Except for the irradiation step, the procedure will be substantially the same as for the photoactivation.

13. Chemical Amplification Using an Organometallic Complex as the Crosslinker Another class of crosslinking agents that are useful for covalently crosslinking two probes comprises organometallic complexes. Activation of the metal complex may be photonic, and the activated complex may then react by substitution with an appropriate reactant situated on the opposite strand in the stem, and the two probes are covalently crosslinked as a result of the new bond formed.

For example, cyclopentadienyl manganese(I) complexes, $CpMnL_3$, where L is a neutral two electron donor ligand such as CO, are useful for their rich photochemical reactivity. These complexes, in contrast, are inert to thermal substitution reaction conditions and thus provide a system that selectively responds to photonic activation. Photoirradiation using 300–350 nm light induces the loss of a CO ligand. The intermediate, $CpMnL_2$, can recombine with the extruded ligand or react with another suitable ligand, L', such as a phosphine, phosphite, amine, ether, olefin, etc. The photoreactivity of the newly formed compound depends on the identity of the new ligand. When L' is a phosphine or phosphite any subsequent reactions proceed with loss of another CO ligand; the phosphine or phosphite remains bound to the metal. In contrast, for most other ligands L' it is this ligand that is photosubstituted upon further reaction. Example. Probes with the following sequences are prepared:

NAXM 011(SEQ ID NO: 58)
5'-GATACGACGCCGCAAAAGCTCTTC<u>ATMAG</u>
NAXM 012 (SEQ ID NO:59)
5'-CT<u>LATCCAAGCCGAGTCTACAGTTATAGG</u>
NAXM 013 (SEQ ID NO:60)
5'-CCTATAACTGTAGACTCGGCTTGGGAAGAG
  CTTTTGCGGCGTCGTATC

M=cyclopentadienylmanganese(I) tricarbonyl
L=trialkylphosphite

Underlined bases comprise the stem-forming portion of the oligonucleotide

Preparation of NAXM 011. Lithium cyclopentadienide is condensed with 2,2-dimethyl-1,3-dioxolane-4-methyl mesylate. The trimethyltin adduct of the cyclopentadiene derivative is reacted with $Mn(CO)_5Br$ to yield 2,2-dimethyl-1,3-dioxolane-4-methylcyclopentadienylmanganese tricarbonyl. The ketal is hydrolyzed to produce 1-(cyclopentadienylmanganese tricarbonyl)-2,3-propanediol. The diol is converted to the 3-O-dimethoxytrityl-2-O-phosphoramidite derivative and the title modified oligonucleotide is prepared by automated DNA synthesis techniques.

Preparation of NAXM 012

The di-t-butylsilylene of 1,1,1-tris(hydroxymethyl)ethane is prepared and the third hydroxyl group is protected as the p-nitrobenzyl ether. The silylene is selectively hydroyzed using tributylammonium fluoride to produce 2-methyl-2-(methyl p-nitrobenzyl ether)-1,3-propanediol. The diol is converted to the 1-O-dimethoxytrityl-3-O-phosphoramidite derivative and the title sequence is prepared by automated DNA synthesis techniques. The oligo is cleaved from the solid support without removing the protecting groups from the exocyclic amines or the phosphate groups. The solution is irradiated with 320 nm light to remove the p-nitrobenzyl ether protecting group. The oligo is lyophilized, dissolved in anhydrous acetonitrile and reacted with diethyl chlorophosphite. The oligonucleotide is then fully deprotected by treatment with 40% aqueous ammonia, isolated by reverse phase HPLC and purified by passage through a Sephadex G25 column.

The Ability to form Crosslinks via a Templated Photosubstitution Reaction.

| Component, | | Sample [mL] | | | | | | | | |
|---|---|---|---|---|---|---|---|---|---|---|
| NAXM | pmol/mL | 1 | 2 | 3 | 4 | 5 | 6 | 7 | 8 | 9 |
| $^{32}P$-011 | 0.2 | | | | | 1 | 1 | 1 | | |
| $^{32}P$-012 | 0.2 | 1 | 1 | | | | | | 1 | |
| $^{32}P$-013 | 0.2 | | | 1 | 1 | | | | | 1 |
| 011 | 1 | | 1 | | 1 | | | | 1 | 1 |
| 012 | 1 | | | 1 | | 1 | | 1 | | 1 |
| 013 | 1 | 1 | | | | | 1 | 1 | 1 | |
| $H_2O$ | | 11 | 11 | 11 | 11 | 11 | 11 | 10 | 10 | 10 |

Protocol:

Add 1 mL of 50 mM 2-aminoethanol to each sample, loaded in a 96-well microtitre plate.

Add 18.5 mL of 1:3 0.75M NaOH: 1×TE (pH 7.5) to each sample

Add 17.5 mL of neutralization buffer (1.75 mL of 3.5% BSA, 1.5 mL of 1.5 M HOAc, 11.3 mL of 20×SSC, and 2.15 mL of water) to each sample. Add 60 mL mineral oil to prevent evaporation.

Incubate at 40° C. for 15 minutes.

Irradiate at 40° C. for 20 minutes using UV-A lamps (sharp cut-off filter at 300 nm)

Analyze by denaturing PAGE (15% with 7 M urea)

The Effect of Thermal Cycling on the Amount of Crosslinked Product Formed

| Component, | | Sample [mL] | | | | | | | |
|---|---|---|---|---|---|---|---|---|---|
| NAXM | pmol/mL | 1 | 2 | 3 | 4 | 5 | 6 | 7 | 8 |
| $^{32}P$-012 | 0.2 | 1 | 1 | 1 | 1 | 1 | 1 | 1 | 1 |
| 013 | 0.01 | | | 1 | 1 | | | 1 | 1 |
| 011 | 1 | 1 | 1 | 1 | 1 | 1 | 1 | 1 | 1 |
| 012 | 1 | 1 | 1 | 1 | 1 | 1 | 1 | 1 | 1 |
| $H_2O$ | | 10 | 10 | 9 | 9 | 10 | 10 | 9 | 9 |
| No. cycles | | 1 | 2 | 1 | 2 | 5 | 5 | 5 | 5 |
| thermal treat. | | + | D | + | D | + | D | + | D |

+ = isothermal, no denaturation
D = samples denatured each cycle

Protocol:

The sample preparation is the same as above. After an initial incubation for 10 minutes at 40° C. the samples were treated as indicated in the table.

Cycle:

Irradiate at 40° C. for 10 minutes

Heat to 85° C. for 2 minutes

Incubate at 40° C. for 10 minutes

Repeat the cycle procedure the indicated number of times, ending with the irradiation step at that cycle number.

Analyze by denaturing PAGE (15%, with 7 M urea)

It is evident from the above results that the subject methodology provides a convenient and efficient way to identify the presence of specific nucleic acid sequences. Amplification is achieved in the absence of enzyme, using chemical reactions to cross-link two probes tethered together by means of a template. Once the two probes have been cross-linked, they in turn may serve as a template for homologous sequences. In this way, a geometric expansion of cross-linked probes may be obtained in relation to a target sequence. Use of the subject automatic devices for performing the subject assays provides for minimization of error introduction and improved consistency in assay conditions.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An automatic device with means for detecting a target nucleic acid sequence in a sample by a method employing at least one pair of probes characterized by having sequences homologous to adjacent portions of said target nucleic acid sequence and having side chains which non-covalently bind to form a stem upon base pairing of said probes to said target nucleic acid sequence, at least one of said side chains having a photoactivatable group, which upon activation during stem formation forms a covalent cross-link with the other side chain member of said stem, where in said method said sample and said probes are combined in an assay medium under base-pairing conditions, said photoactivatable groups are activated resulting in cross-linked pairs of probes and said cross-linked pairs of probes are detected as indicative of the presence of said target sequence in said sample, said device comprising:
  a means for modulating the base pairing conditions of said assay medium; and
  a control circuit responsive to the base pairing conditions of said medium and configured to actuate an irradiation source for said photoactivatable group at a predetermined assay medium condition.

2. The device according to claim 1 wherein the base pairing conditions of said assay medium is the temperature of said medium.

3. An automatic device with means for detecting a target nucleic acid sequence in a sample by a method employing at least one pair of probes characterized by having sequences homologous to adjacent portions of said target nucleic acid sequence and having side chains which non-covalently bind to form a stem upon base pairing of said probes to said target nucleic acid sequence, at least one of said side chains having a photoactivatable group, which upon activation during stem formation forms a covalent cross-link with the other side chain member of said stem, where in said method said sample and said probes are combined in an assay medium under base-pairing conditions, said photoactivatable groups are activated resulting in cross-linked pairs of probes and said cross-linked pairs of probes are detected as indicative of the presence of said target sequence in said sample, said device comprising:
  a thermal cycler for modulating the temperature of said assay medium;
  a control circuit responsive to the temperature of said assay medium and configured to actuate an irradiation source for activating said photoactivatable group when said temperature is below a first predetermined temperature; and an assay containment means for holding said assay medium.

4. The device according to claim 3, wherein said control circuit comprises a thermistor for transducing the temperature of said assay medium into an electrical signal.

5. The device according to claim 4, wherein said control circuit is configured so that said irradiation source is inactivated at a second predetermined temperature, wherein said second predetermined temperature is a temperature below said first predetermined temperature.

* * * * *

```
                         SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "probe"

(xi) SEQUENCE DESCRIPTION: SEQ ID NO:1:

GTTTTTCTTG TTGAACAAAA ATCCT                                              25

(2) INFORMATION FOR SEQ ID NO:2:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "probe"

(xi) SEQUENCE DESCRIPTION: SEQ ID NO:2:

TTTCTAGGGG GAACACCCGT GTGTCT                                             26

(2) INFORMATION FOR SEQ ID NO:3:

(i) SEQUENCE CHARACTERISTICS:
          (A) LENGTH: 60 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "probe"

(xi) SEQUENCE DESCRIPTION: SEQ ID NO:3:

CTGGGAAACA TCAAAGGAAT TCTCGGAAAG AAAGCCAGCA GTCTCCTCTT TACAGAAAAG        60

(2) INFORMATION FOR SEQ ID NO:4:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "probe"
```

(xi) SEQUENCE DESCRIPTION: SEQ ID NO:4:

CATAGGGGAT ACCAGACAAT TCAAAC                                              26

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:5:

ACCTGACCGT GCGCCCTTCA CAAAG                                               25

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:6:

ACGATGCCGC CATCCTCCTG CAAAA                                               25

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:7:

CACAGACCAT TCGCAGTATT GAAAAC                                              26

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:8:

ATTTTGTCTT TGCGCACAGA CGATCTATTT                                          30

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:9:

AAATAGATCG TCTGTTTGCT TT                                                              22

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 1..20
        (D) OTHER INFORMATION: /label= N
            /note= "N=ethoxycoumarin"

(xi) SEQUENCE DESCRIPTION: SEQ ID NO:10:

ANAGCGCGCA AAGACAAAAT                                                                 20

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:11:

ATTTTGTCTT TGCGCGGCTT T                                                               21

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 21
        (D) OTHER INFORMATION: /note= "N=ethoxycoumarin"

(xi) SEQUENCE DESCRIPTION: SEQ ID NO:12:

AAATAGATCG TCTGTTTGCA NA                                                              22

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:13:

TTTGCGCGCA AAGACAAAAT                                                                 20

(2) INFORMATION FOR SEQ ID NO:14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:14:

TTTATAAAAA GCTCGTAATA TGCAAGAGCA TTGTAAGCAG AAGACTTA        48

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:15:

TTTATAAAAA GCTCGTAATA TGCTTTTTTT TT        32

(2) INFORMATION FOR SEQ ID NO:16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:16:

TAAGTCTTCT GCTTACAATG CTCTTTTTTT TT        32

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 2
        (D) OTHER INFORMATION: /note= "N=ethoxycoumarin"

(xi) SEQUENCE DESCRIPTION: SEQ ID NO:17:

ANAGCATATT ACGAGCTTTT TATAAA        26

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

```
    (ix) FEATURE:
         (A) NAME/KEY: misc_feature
         (B) LOCATION: 2
         (D) OTHER INFORMATION: /note= "N = ethoxycoumarin"

(xi) SEQUENCE DESCRIPTION: SEQ ID NO:18:

ANAAAGCATA TTACGAGCTT TTTATAAA                                                28

(2) INFORMATION FOR SEQ ID NO:19:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "probe"

(ix) FEATURE:
         (A) NAME/KEY: misc_feature
         (B) LOCATION: 5
         (D) OTHER INFORMATION: /note= "N=ethoxycoumarin"

(xi) SEQUENCE DESCRIPTION: SEQ ID NO:19:

AAAANAAGCA TATTACGAGC TTTTTATAAA                                              30

(2) INFORMATION FOR SEQ ID NO:20:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "probe"

(ix) FEATURE:
         (A) NAME/KEY: misc_feature
         (B) LOCATION: 2
         (D) OTHER INFORMATION: /note= "N=ethoxycoumarin"

(xi) SEQUENCE DESCRIPTION: SEQ ID NO:20:

ANAAAAAGCA TATTACGAGC TTTTTATAAA                                              30

(2) INFORMATION FOR SEQ ID NO:21:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "probe"

(xi) SEQUENCE DESCRIPTION: SEQ ID NO:21:

TAAGTCTTCT GCTTACAATG CTCTTGCATA TTACGAGCTT TTTATAAA                          48

(2) INFORMATION FOR SEQ ID NO:22:

(i) SEQUENCE CHARACTERISTICS:
         (A) LENGTH: 49 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "probe"

(xi) SEQUENCE DESCRIPTION: SEQ ID NO:22:
```

```
TAAGTCTTCT GCTTACAATG AACTTGCATA TTACGAGCTT TTTATAAAT                    49
```

(2) INFORMATION FOR SEQ ID NO:23:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:23:

```
TTTTTTTTTC TTGCATATTA CGAGCTTTTT ATAAA                                   35
```

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:24:

```
TTTTTTTTTC ATTGTAAGCA GAAGACTTA                                          29
```

(2) INFORMATION FOR SEQ ID NO:25:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 29
        (D) OTHER INFORMATION: /note= "N=ethoxycoumarin"

(xi) SEQUENCE DESCRIPTION: SEQ ID NO:25:

```
TTTATAAAAA GCTCGTAATA TGCAAGAANA AAA                                     33
```

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 28
        (D) OTHER INFORMATION: /note= "N=ethoxycoumarin"

(xi) SEQUENCE DESCRIPTION: SEQ ID NO:26:

```
TTTATAAAAA GCTCGTAATA TGCAAGANAA AAA                                     33
```

(2) INFORMATION FOR SEQ ID NO:27:

(i) SEQUENCE CHARACTERISTICS:
    (A) LENGTH: 54 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "probe"

(xi) SEQUENCE DESCRIPTION: SEQ ID NO:27:

GATATCGGAT TTACCAAATA CGGCGGGCCC GCCGTTAGCT AACGCTAATC GATT        54

(2) INFORMATION FOR SEQ ID NO:28:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 6
        (D) OTHER INFORMATION: /note= "N=ethoxycoumarin"

(xi) SEQUENCE DESCRIPTION: SEQ ID NO:28:

AAAAANAGCC GTTAGCTAAC GCTAATCGAT T        31

(2) INFORMATION FOR SEQ ID NO:29:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:29:

GATATCGGAT TTACCAAATA CGGCGGGCCC TTTTTTT        37

(2) INFORMATION FOR SEQ ID NO:30:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 6
        (D) OTHER INFORMATION: /note= "N=ethoxycoumarin"

(xi) SEQUENCE DESCRIPTION: SEQ ID NO:30:

AAAAANAGCC GTATTTGGTA AATCCGATAT C        31

(2) INFORMATION FOR SEQ ID NO:31:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "probe"

(xi) SEQUENCE DESCRIPTION: SEQ ID NO:31:

AATCGATTAG CGTTAGCTAA CGGCGGGCCC TTTTTTT                                37

(2) INFORMATION FOR SEQ ID NO:32:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(ix) FEATURE:
            (A) NAME/KEY: misc_feature
            (B) LOCATION: 4
            (D) OTHER INFORMATION: /note= "N=ethoxycoumarin"

(xi) SEQUENCE DESCRIPTION: SEQ ID NO:32:

AAANAAGCCG TTAGCTAACG CTAATCGATT                                        30

(2) INFORMATION FOR SEQ ID NO:33:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(ix) FEATURE:
            (A) NAME/KEY: misc_feature
            (B) LOCATION: 3
            (D) OTHER INFORMATION: /note= "N=ethoxycoumarin"

(xi) SEQUENCE DESCRIPTION: SEQ ID NO:33:

AANAAAGCCG TTAGCTAACG CTAATCGATT                                        30

(2) INFORMATION FOR SEQ ID NO:34:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "probe"

(ix) FEATURE:
            (A) NAME/KEY: misc_feature
            (B) LOCATION: 2
            (D) OTHER INFORMATION: /note= "N=ethoxycoumarin"

(xi) SEQUENCE DESCRIPTION: SEQ ID NO:34:

ANAAAAGCCG TTAGCTAACG CTAATCGATT                                        30

(2) INFORMATION FOR SEQ ID NO:35:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid (A) DESCRIPTION: /desc = "probe"

(ix) FEATURE:
        (A) NAME/KEY: misc_feature
        (B) LOCATION: 1
        (D) OTHER INFORMATION: /note= "N=ethoxycoumarin"

(xi) SEQUENCE DESCRIPTION: SEQ ID NO:35:

NAAAAAGCCG TTAGCTAACG CTAATCGATT                                              30

(2) INFORMATION FOR SEQ ID NO:36:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO:36:

GATTTAAAAA CCAAGGTCGA TGTGATAGGG CTCGTATGTG GAATGTCGAA CTCATCGGCG            60
AT                                                                            62

(2) INFORMATION FOR SEQ ID NO:37:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 9
        (D) OTHER INFORMATION: /note= "N=ethoxycoumarin"

(xi) SEQUENCE DESCRIPTION: SEQ ID NO:37:

GGGCGAGANA TATCACATCG ACCTTGGTTT TTAAATC                                     37

(2) INFORMATION FOR SEQ ID NO:38:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 36
        (D) OTHER INFORMATION: /note= "N=ethoxycoumarin"

(xi) SEQUENCE DESCRIPTION: SEQ ID NO:38:

GATTTAAAAA CCAAGGTCGA TGTGATAGGG CTCGANAAAA A                                41

(2) INFORMATION FOR SEQ ID NO:39:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
             (A) DESCRIPTION: /desc = "probe"

(xi) SEQUENCE DESCRIPTION: SEQ ID NO:39:

TCGCCGATGA GTTCGACATT CCACATACGA GCCCTTTCTC G                         41

(2) INFORMATION FOR SEQ ID NO:40:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(xi) SEQUENCE DESCRIPTION: SEQ ID NO:40:

TTTTTTTTAT GTGGAATGTC GAACTCATCG GCGA                                 34

(2) INFORMATION FOR SEQ ID NO:41:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(ix) FEATURE:
             (A) NAME/KEY: misc_feature
             (B) LOCATION: 30
             (D) OTHER INFORMATION: /note= "N=biotin"

(xi) SEQUENCE DESCRIPTION: SEQ ID NO:41:

TTTTTTCCAA GGAGGTAAAC GCTCCTCTGN                                      30

(2) INFORMATION FOR SEQ ID NO:42:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(ix) FEATURE:
             (A) NAME/KEY: misc_feature
             (B) LOCATION: 1
             (D) OTHER INFORMATION: /note= "N=fluorescein"

(ix) FEATURE:
             (A) NAME/KEY: misc_feature
             (B) LOCATION: 27
             (D) OTHER INFORMATION: /note= "N=ethoxycoumarin"

(xi) SEQUENCE DESCRIPTION: SEQ ID NO:42:

NATTGGTTGA TCGCCCAGAC AATGCANA                                        28

(2) INFORMATION FOR SEQ ID NO:43:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: other nucleic acid

```
            (A) DESCRIPTION: /desc = "probe"

(ix) FEATURE:
            (A) NAME/KEY: misc_feature
            (B) LOCATION: 30
            (D) OTHER INFORMATION: /note= "N=biotin"

(xi) SEQUENCE DESCRIPTION: SEQ ID NO:43:

TTTTTTTCCC TTTATACGCT CAAGCAATAN                                              30

(2) INFORMATION FOR SEQ ID NO:44:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 1
        (D) OTHER INFORMATION: /note= "n=fluorescein"

(ix) FEATURE:
        (A) NAME/KEY: misc_feature
        (B) LOCATION: 27
        (D) OTHER INFORMATION: /note= "N=ethoxycoumarin"

(xi) SEQUENCE DESCRIPTION: SEQ ID NO:44:

NTCTTTGCTA TAGCACTATC AAGCCANA                                                28

(2) INFORMATION FOR SEQ ID NO:45:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 30
        (D) OTHER INFORMATION: /note= "N=biotin"

(xi) SEQUENCE DESCRIPTION: SEQ ID NO:45:

TTTTTTGTCT CGAACATCTG AAAGCATGGN                                              30

(2) INFORMATION FOR SEQ ID NO:46:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 1
        (D) OTHER INFORMATION: /note= "N=fluorescein"

(ix) FEATURE:
        (A) NAME/KEY: misc_feature
        (B) LOCATION: 27
        (D) OTHER INFORMATION: /note= "N=ethoxycoumarin"
```

(xi) SEQUENCE DESCRIPTION: SEQ ID NO:46:

NCTGCGTCTT GCTCTATTTG ACCGCANA                                    28

(2) INFORMATION FOR SEQ ID NO:47:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "probe"

(ix) FEATURE:
         (A) NAME/KEY: misc_feature
         (B) LOCATION: 30
         (D) OTHER INFORMATION: /note= "n=biotin"

(xi) SEQUENCE DESCRIPTION: SEQ ID NO:47:

TTTTTTTGAG CGGCTCTGTC ATTTGCCCAN                                  30

(2) INFORMATION FOR SEQ ID NO:48:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "probe"

(ix) FEATURE:
         (A) NAME/KEY: misc_feature
         (B) LOCATION: 1
         (D) OTHER INFORMATION: /note= "N=fluorescein"

(ix) FEATURE:
         (A) NAME/KEY: misc_feature
         (B) LOCATION: 27
         (D) OTHER INFORMATION: /note= "N=ethoxycoumarin"

(xi) SEQUENCE DESCRIPTION: SEQ ID NO:48:

NTGTCCAAGG ATTATTTGCT GGTCCANA                                    28

(2) INFORMATION FOR SEQ ID NO:49:

(i) SEQUENCE CHARACTERISTICS:
         (A) LENGTH: 62 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "probe"

(xi) SEQUENCE DESCRIPTION: SEQ ID NO:49:

ATCGCCGATG AGTTCGACAT TCCACATACG AGCCCTATCA CATCGACCTT GGTTTTTAAA  60

TC                                                                62

(2) INFORMATION FOR SEQ ID NO:50:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "probe"

(xi) SEQUENCE DESCRIPTION: SEQ ID NO:50:

AAAGGGCTCG AAAAA                                                               15

(2) INFORMATION FOR SEQ ID NO:51:

(i) SEQUENCE CHARACTERISTICS:
             (A) LENGTH: 46 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(xi) SEQUENCE DESCRIPTION: SEQ ID NO:51:

TCTTTATTTA GATATAGAAT TTCTTTTTTA GAGAGTTTAG AAGAAT                              46

(2) INFORMATION FOR SEQ ID NO:52:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(xi) SEQUENCE DESCRIPTION: SEQ ID NO:52:

ATTCTTCTAA ACTCTCTAAA AAACAAGGAA                                                30

(2) INFORMATION FOR SEQ ID NO:53:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(ix) FEATURE:
             (A) NAME/KEY: misc_feature
             (B) LOCATION: 2
             (D) OTHER INFORMATION: /note=
                 "N=2'-deoxy-5-(b-aminoethoxymethyl)uridine"

(ix) FEATURE:
             (A) NAME/KEY: misc_feature
             (B) LOCATION: 5
             (D) OTHER INFORMATION: /note=
                 "N=2'-deoxy-5(b-aminoethoxymethyl)uridine"

(xi) SEQUENCE DESCRIPTION: SEQ ID NO:53:

TNCCNTGGAA ATTCTATATC TAAATAAAGA                                                30

(2) INFORMATION FOR SEQ ID NO:54:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(xi) SEQUENCE DESCRIPTION: SEQ ID NO:54:

ATTCTTCTAA ACTCTCTAAA AAACAAGAA                                                 29

(2) INFORMATION FOR SEQ ID NO:55:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 2
        (D) OTHER INFORMATION: /note=
            "N=2'-deoxy-5-(b-aminoethoxymethyl)uridine"

(ix) FEATURE:
        (A) NAME/KEY: misc_feature
        (B) LOCATION: 4
        (D) OTHER INFORMATION: /note=
            "N=2'-deoxy-5-(b-aminoethoxymethyl)uridine"

(xi) SEQUENCE DESCRIPTION: SEQ ID NO:55:

TNCNTGGAAA TTCTATATCT AAATAAAGA                            29

(2) INFORMATION FOR SEQ ID NO:56:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 27
        (D) OTHER INFORMATION: /note= "N=Pt or Pd square planar
            complex"

(xi) SEQUENCE DESCRIPTION: SEQ ID NO:56:

ATTCTTCTAA ACTCTCTAAA AAACAANAA                            29

(2) INFORMATION FOR SEQ ID NO:57:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(ix) FEATURE:
        (A) NAME/KEY: misc_feature
        (B) LOCATION: 3
        (D) OTHER INFORMATION: /note= "N=4-thiouridine"

(xi) SEQUENCE DESCRIPTION: SEQ ID NO:57:

TTNTTGGAAA TTCTATATCT AAATAAAGA                            29

(2) INFORMATION FOR SEQ ID NO:58:

(i) SEQUENCE CHARACTERISTICS:
        (A) LENGTH: 29 base pairs
        (B) TYPE: nucleic acid
        (C) STRANDEDNESS: single
        (D) TOPOLOGY: linear

```
        (ii) MOLECULE TYPE: other nucleic acid
             (A) DESCRIPTION: /desc = "probe"

(ix) FEATURE:
             (A) NAME/KEY: misc_feature
             (B) LOCATION: 27
             (D) OTHER INFORMATION: /note=
                 "N=cyclopentadienylmanganese(I)tricarbonyl"

(xi) SEQUENCE DESCRIPTION: SEQ ID NO:58:

GATACGACGC CGCAAAAGCT CTTCATNAG                                                29

(2) INFORMATION FOR SEQ ID NO:59:

(i) SEQUENCE CHARACTERISTICS:
             (A) LENGTH: 29 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(ix) FEATURE:
             (A) NAME/KEY: misc_feature
             (B) LOCATION: 3
             (D) OTHER INFORMATION: /note= "N=trialkylphosphate"

(xi) SEQUENCE DESCRIPTION: SEQ ID NO:59:

CTNATCCAAG CCGAGTCTAC AGTTATAGG                                                29

(2) INFORMATION FOR SEQ ID NO:60:

(i) SEQUENCE CHARACTERISTICS:
             (A) LENGTH: 48 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "probe"

(xi) SEQUENCE DESCRIPTION: SEQ ID NO:60:

CCTATAACTG TAGACTCGGC TTGGGAAGAG CTTTTGCGGC GTCGTATC                           48
```